(12) United States Patent
Thornton

(10) Patent No.: US 11,142,568 B2
(45) Date of Patent: Oct. 12, 2021

(54) ANTIBODY

(71) Applicant: The University of Exeter

(72) Inventor: Christopher Thornton, Exeter (GB)

(73) Assignee: THE UNIVERSITY OF EXETER, Exeter (GB)

( * ) Notice: Subject to any disclaimer, the term of this patent is extended or adjusted under 35 U.S.C. 154(b) by 0 days.

(21) Appl. No.: 16/518,565

(22) Filed: Jul. 22, 2019

(65) Prior Publication Data

US 2020/0024332 A1 Jan. 23, 2020

Related U.S. Application Data

(63) Continuation of application No. 15/465,264, filed on Mar. 21, 2017, now abandoned, which is a continuation of application No. 14/298,695, filed on Jun. 6, 2014, now abandoned, which is a continuation of application No. 13/144,872, filed as application No. PCT/GB2010/000064 on Jan. 18, 2010, now abandoned.

(60) Provisional application No. 61/145,282, filed on Jan. 16, 2009.

(51) Int. Cl.
*C07K 16/14* (2006.01)
*G01N 33/569* (2006.01)

(52) U.S. Cl.
CPC ....... *C07K 16/14* (2013.01); *G01N 33/56961* (2013.01); *C07K 2317/56* (2013.01); *C07K 2317/565* (2013.01); *G01N 2333/38* (2013.01); *G01N 2469/20* (2013.01)

(58) Field of Classification Search
None
See application file for complete search history.

(56) References Cited

PUBLICATIONS

Christopher R. Thornton, et al., "A One-Step, Immunochromatographic Lateral Flow Device Specific to Rhizoctonia solani and Certain Related Species, and Its Use to Detect and Quantify R. solani in Soil", Techniques, Publication No. P-2004-0112-02R, 2004, The American Phytopathological Society, Phytopathology, vol. 94, No. 3, pp. 280-288.

Thornton, Christopher R. "Development of an immunochromatic lateral-flow device for rapid serodiagnosis of invasive aspergillosis", Clinical and Vaccine Immunology, vol. 15, No. 7, Jul. 2008 (Jul. 2008), pp. 1095-1105, XP007912963, ISSN: 1556-6811.
Hao Wei et al. "Well-characterized monoclonal antibodies against cell wall antigen of *Aspergillus* species improve immunoassay specificity and sensitivity", Clinical and Vaccine Immunology, vol. 15, No. 2, Feb. 2008 (Feb. 2008), pp. 194-202, XP007912983, ISSN: 1556-6811.
Chong Ken T K et al. "AFMP2 encodes a novel immunogenic protein of the antigenic mannoprotein superfamily in Aspergillus fumigatus", Journal of Clinical Microbiology May 2004 LNKD-PUBMED: 15131215, vol. 42, No. 5, May 2004 (May 2004), pp. 2287-2291, XP007912988, ISSN: 0095-1137.
Woo Patrick C Y et al. "Detection of cell wall galactomannoprotein Afmp1p in culture supernatants of Aspergillus fumigatus and in sera of aspergillosis patients", Journal of Clinical Microbiology Nov. 2002 LNKD-PUBMED: 12409437, vol. 40, No. 11, Nov. 2002 (Nov. 2002), pp. 4382-4387, XP007912972. ISSN: 0095-1137.
Wiederhold Nathan P et al.: "Comparison of Lateral Flow Technology and Galactomannan and (1->3)-beta-D-Glucan Assays for Detection of Invasive Pulmonary Aspergillosis", Clinical and Vaccine Immunology, vol. 16, No. 12, Dec. 2009 (Dec. 2009), pp. 1844-1846, XP007912962.
Thornton CR: "Detection of Invasive Aspergillosis" In: Laskin AI et al.: "Advances in Applied Microbiology", 2010, Elsevier Academic Press, XP008122251, ISBN: 9780123809919 vol. 70, pp. 187-216.
Pazos Carmen et al: "Contribution of (1->3)-beta-D-glucan chromogenic assay to diagnosis and therapeutic monitoring of invasive aspergillosis in neutropenic adult patentis: a comparsion with serial screening for circulating galactomannan." Journal of Clinical Microbiology Jan. 2005 LNKD-PUBMED: 15634986, vol. 43, No. 1, Jan. 2005 (Jan. 2005), pp. 299-305, XP007912964, ISSN: 0095-1137.
Mennink-Kersten M A et al: "Detection of circulating galactomannan for the diagnosis and management of invasive aspergillosis", Lancet Infectious Diseases, Elsevier Ltd, US LNKD-DOI:10.1016/S1473-3099(04)01045-x, vol. 4, No. 6, Jun. 1, 2004 (Jun. 1, 2004), pp. 349-357, XP004808605, ISSN: 1473-3099.
Extended European Search Report of EP19186058.4 dated Jan. 10, 2020.
Minutes of the Oral Proceedings from the Board of Appeals of the European Patent Office dated Jul. 24, 2019.
Decision from the Board of Appeals of the European Patent Office dated Sep. 19, 2019.

*Primary Examiner* — Brian Gangle
(74) *Attorney, Agent, or Firm* — Seyfarth Shaw LLP; Jamaica P. Szeliga

(57) ABSTRACT

The invention relates to antibodies to *Aspergillus* species and to methods of producing those antibodies. The invention also relates to the use of such antibodies in identifying the presence of the *Aspergillus* species and to methods of treating an infection with the *Aspergillus* species.

3 Claims, 11 Drawing Sheets
Specification includes a Sequence Listing.

Figure 1

ATGGATTTTGGGCTGATTTTTTTATTGTTGCTCTTTTAAAAGGGGTCCAGTGTGA
GGTGAAGCTTCTCGAGTCTGGAGGTGGCCTGGTGCAGCCTGGAGGATCCCTGAA
ACTCTCCTGTGCAGCCTCAGGATTCGATTTAGTAGATACTGGATGAGTTGGGTC
CGGCAGGCTCCAGGGAAGGGCTAGAATGGATTGGAGAAATTAATCCAGATAGC
AGTAAGATAAACTATATGCCATCTCTAAAGGATAAATTCATCATCTCCAGAGACA
ACGCCAAAAATACGCTGTACCTGCAAATGAGCAAAGTGAGATCTGAGGACACAG
CCCTTTATTACTGTGCAAGACCTCGGGGTTACTACGCTATGGACTTCTGGGGTCA
AGGAACCTCAGTCACCGTCTCCTCAGCTACAACAACAGCCCCATCCGTCTTCCCC
CTGGCAC

Figure 2

MDFGLIFFIVALLKGVQCEVKLLESGGGLVQPGGSLKLSCAASGFDFX$_n$SRYWMSWV
RQAPGKGLEWIGEINPDX$_n$SSKINYMPSLKDKFIISRDNAKNTLYLQMSKVRSEDTAL
YYCARPRGYX$_n$YAMDFWGQGTSVTVSSATTTAPSVFPLA

Figure 3

ATGGATTTTGGGCTGATTTTTTTATTGTTGCTCTTTTAAAAGGGGTCCAGTGTGA
GGTGAAGCTTCTCGAGTCTGGAGGTGGCCTGGTGCAGCCTGGAGGATCCCTGAA
ACTCTCCTGTGCAGCCTCAGGATTCGATTTAGTAGATACTGGATGAGTTGGGTC
CGGCAGGCTCCAGGGAAGGGCTAGAATGGATTGGAGAAATTAATCCAGATAGC
AGTAAGATAAACTATATGCCATCTCTAAAGGATAAATTCATCATCTCCAGAGACA
ACGCCAAAAATACGCTGTACCTGCAAATGAGCAAAGTGAGATCTGAGGACACAG
CCCTTTATTACTGTGCAAGACCTCGGGGTTACTACGCTATGGACTTCTGGGGTCA
AGGAACCTCAGTCACCGTCTCCTCAGCTACAACAACAGCCCCATCCGTCTTCCCC
CTGGCAC

Figure 4

MDFGLIFFIVALLKGVQCEVKLLESGGGLVQPGGSLKLSCAASGFDFX$_n$SRYWMSWV
RQAPGKGLEWIGEINPDX$_n$SSKINYMPSLKDKFIISRDNAKNTLYLQMSKVRSEDTAL
YYCARPRGYX$_n$YAMDFWGQGTSVTVSSATTTAPSVFPLA

Figure 5

ATGGATTTTGGGCTGATTTTTTTATTGTTGCTCTTTTAAAAGGGGTCCAGTGTGA
GGTGAAGCTTCTCGAGTCTGGAGGTGGCCTGGTGCAGCCTGGAGGATCCCTGAA
ACTCTCCTGTGCAGCCTCAGGATTCGATTTAGTAGATACTGGATGAGTTGGGTC
CGGCAGGCTCCAGGGAAGGGCTAGAATGGATTGGAGAAATTAATCCAGATAGC
AGTAAGATAAACTATATGCCATCTCTAAAGGATAAATTCATCATCTCCAGAGACA
ACGCCAAAAATACGCTGTACCTGCAAATGAGCAAAGTGAGATCTGAGGACACAG
CCCTTTATTACTGTGCAAGACCTCGGGGTTACTACGCTATGGACTTCTGGGGTCA
AGGAACCTCAGTCACCGTCTCCTCAGCTACAACAACAGCCCCATCCGTCTTCCCC
CTGGCAC

Figure 6

MDFGLIFFIVALLKGVQCEVKLLESGGGLVQPGGSLKLSCAASGFDFX$_n$SRYWMSWV
RQAPGKGLEWIGEINPDX$_n$SSKINYMPSLKDKFIISRDNAKNTLYLQMSKVRSEDTAL
YYCARPRGYX$_n$YAMDFWGQGTSVTVSSATTTAPSVSPWR

Figure 7

ATGGATTTTGGGCTGATTTTTTTTATTGTTGCTCTTTTAAAAGGGGTCCAGTGTGA
GGTGAAGCTTCTCGAGTCTGGAGGTGGCCTGGTGCAGCCTGGAGGATCCCTGAA
ACTCTCCTGTGCAGCCTCAGGATTCGATTTAGTAGATACTGGATGAGTTGGGTC
CGGCAGGCTCCAGGGAAAGGGCTAGAATGGATTGGAGAAATTAATCCAGATGGC
AGTAAGATAAACTATATGCCATCTCTAAAGGATAAATTCATCATCTCCAGAGACA
ACGCCAAAAATACGCTGTACCTGCAAATGAGCAAAGTGAGATCTGAGGACACAG
CCCTTTATTACTGTGCAAGACCTCGGGGTTACTACGCTATGGACTTCTGGGGTCA
AGGAACCTCAGTCACCGTCTCCTCAGCTACAACAACAGCCCCACCCGTCTATCCA
CTGGTCCCTGAAGCTTGGG

Figure 8

MDFGLIFFIVALLKGVQCEVKLLESGGGLVQPGGSLKLSCAASGFDFX$_n$SRYWMSWV
RQAPGKGLEWIGEINPDX$_n$GSKINYMPSLKDKFIISRDNAKNTLYLQMSKVRSEDTAL
YYCARPRGYX$_n$YAMDFWGQGTSVTVSSATTTAPPVYPLVPEAW

Figure 9

ATGGATTTTGGGCTGATTTTTTTTATTGTTGCTCTTTTAAAAGGGGTCCAGTGTGA
GGTGAAGCTTCTCGAGTCTGGAGGTGGCCTGGTGCAGCCTGGAGGATCCCTGAA
ACTCTCCTGTGCAGCCTCAGGATTCGATTTAGTAGATACTGGATGAGTTGGGTC
CGGCAGGCTCCAGGGAAAGGGCTAGAATGGATTGGAGAAATTAATCCAGATAGC
AGTAAGATAAACTATATGCCATCTCTAAAGGATAAATTCATCATCTCCAGAGACA
ACGCCAAAAATACGCTGTACCTGCAAATGAGCAAAGTGAGATCTGAGGACACAG
CCCTTTATTACTGTGCAAGACCTCGGGGTTACTACGCTATGGACTTCTGGGGTCA
AGGAACCTCAGTCACCGTCTCCTCAGCTACAACAACAGCCCCACCCGTCTATCCC
CTGGCCCCTGG

Figure 10

MDFGLIFFIVALLKGVQCEVKLLESGGGLVQPGGSLKLSCAASGFDFX$_n$SRYWMSWV
RQAPGKGLEWIGEINPDX$_n$SSKINYMPSLKDKFIISRDNAKNTLYLQMSKVRSEDTAL
YYCARPRGYX$_n$YAMDFWGQGTSVTVSSATTTAPPVYPLAP

Figure 11

MDFGLIFFIVALLKGVQCEVKLLESGGGLVQPGGSLKLSCAASGFDFX$_n$SRYWMSWV
RQAPGKGLEWIGEINPDX$_n$SSKINYMPSLKDKFIISRDNAKNTLYLQMSKVRSEDTAL
YYCARPRGYX$_n$YAMDFWGQGTSVTVSSATTTAPSVFPLA

Figure 12

ATGGAGTCACATACCCAGGTCTTTATATTCGTGTTTCTCTGGTTGTCTGGTGTTGA
CGGAGACATTGTGATGACCCAGTCTCACAAAGTCATGTCCACATCAGTAGGAGA
CAGGGTCAGCATCACCTGCAAGGCCAGTCAGGATGTGAGTACTGCTGTAGCCTG
GCATCAACAGAAACCAGGACAATCTCCTAAACCACTGATTTACTCGGCATCCTAC
CAGTACACTGGAGTCCCTGATCGCTTCACTGGCAGTGGATCTGGGACGGATTTCA
CTTTCACCATCAGCAGTGTGCAGGCTGAAGACCTGGCAGTTTATTACTGTCAGCA
ACATTACAGTATTCCGTGGACGTTCGGTGGAGGCACCAAGCTGGAAATCAAACG
GGCTGATGCTGCACCAACTGTATCCATCTTCCCACCATCCAGTAAGCTTGGG

Figure 13

MESHTQVFIFVFLWLSGVDGDIVMTQSHKVMSTSVGDRVSITCKASQDVX$_n$STAVA
WHQQKPGQSPKPLIYSAX$_n$SYQYTGVPDRFTGSGSGTDFTFTISSVQAEDLAVYYCQ
QHYSX$_n$IPWTFGGGTKLEIKRADAAPTVSIFPPSSKLG

Figure 14

ATGGAGACACAGTCTCAGGTCTTTGTATTCGTGTTTCTCTGGTTGTCTGGTGTTGA
CGGAGACATTGTGATGACCCAGTCTCACAAAGTCATGTCCACATCAGTAGGAGA
CAGGGTCAGCATCACCTGCAAGGCCAGTCAGGATGTGAGTACTGCTGTAGCCTG
GCATCAACAGAAACCAGGACAATCTCCTAAACCACTGATTTACTCGGCATCCTAC
CAGTACACTGGAGTCCCTGATCGCTTCACTGGCAGTGGATCTGGGACGGATTTCA
CTTTCACCATCAGCAGTGTGCAGGCTGAAGACCTGGCAGTTTATTACTGTCAGCA
ACATTACAGTATTCCGTGGACGTTCGGTGGAGGCACCAAGCTGGAAATCAAACG
GGCTGATGCTGCACCAACTGTATCCATCTTCCCACCATCCAGTAAGCTTGGG

Figure 15

METQSQVFVFVFLWLSGVDGDIVMTQSHKVMSTSVGDRVSITCKASQDVX$_n$STAVA
WHQQKPGQSPKPLIYSAX$_n$SYQYTGVPDRFTGSGSGTDFTFTISSVQAEDLAVYYCQ
QHYSX$_n$IPWTFGGGTKLEIKRADAAPTVSIFPPSSKLG

Figure 16

CCCAGGTCTTTGTATTGGTGTTTCTCTGGTTGTCTGGTGTTGACGGAGACATTGTG
ATGACCCAGTCTCACAAAGTCATGTCCACATCAGTAGGAGACAGGGTCAGCATC
ACCTGCAAGGCCAGTCAGGATGTGAGTACTGCTGTAGCCTGGCATCAACAGAAA
CCAGGACAATCTCCTAAACCACTGATTTACTCGGCATCCTACCAGTACACTGGAG
TCCCTGATCGCTTCACTGGCAGTGGATCTGGGACGGATTTCACTTTCACCATCAG
CAGTGTGCAGGCTGAAGACCTGGCAGTTTATTACTGTCAGCAACATTACAGTATT
CCGTGGACGTTCGGTGGAGGCACCAAGCTGGAAATCAAACGGGCTGATGCTGCA
CCAACTGTATCCATCTTCCCACCATCCAGTAAGCTTGGG

Figure 17

QVFVLVFLWLSGVDGDIVMTQSHKVMSTSVGDRVSITCKASQDVX$_n$STAVAWHQQ
KPGQSPKPLIYSAX$_n$SYQYTGVPDRFTGSGSGTDFTFTISSVQAEDLAVYYCQQHYSX$_n$
IPWTFGGGTKLEIKRADAAPTVSIFPPSSKLG

Figure 18

MESXSQVFVFVFLWLSGVDGDIVMTQSHKVMSTSVGDRVSITCKASQDVX$_n$STAVA
WHQQKPGQSPKPLIYSAX$_n$SYQYTGVPDRFTGSGSGTDFTFTISSVQAEDLAVYYCQ
QHYSX$_n$IPWTFGGGTKLEIKRADAAPTVSIFPPSSKLG

Figure 19

GFDFX$_n$SRYW

Figure 20

QDVX$_n$STA

Figure 21

INPDX$_n$SSKI

Figure 22

INPDX$_n$GSKI

Figure 23

SAX$_n$S

Figure 24

ARPRGYX$_n$YAMDF

Figure 25

QQHYSX$_n$IPWT

ANTIBODY

SEQUENCE LISTING

The instant application contains a Sequence Listing which has been submitted electronically in ASCII format and is hereby incorporated by reference in its entirety. Said ASCII copy, created on Dec. 15, 2020, is named 102943-000005_SL.txt and is 43,625 bytes in size.

FIELD OF THE INVENTION

This invention relates to a method of diagnosing a fungal infection, and to antibodies and related molecules for use in such a method.

BACKGROUND

The dramatic increase in opportunistic infections of humans caused by *Aspergillus* species over the last decade is associated with a rise in the numbers of solid-organ transplants and the use of aggressive cancer therapies and other immuno-modulating treatments (Brakhage, A. A., and K. Langfelder. 2002. Menacing mold; the molecular biology of *Aspergillus fumigatus*. Annu. Rev. Microbiol. 56:433-455; Latgé, J.-P. 1999. *Aspergillus fumigatus* and Aspergillosis. Clin. Microbiol. Rev. 12:310-350). The mortality due to invasive aspergillosis (IA) has increased by 357% over the last 25 years and IA has become one of the leading causes of death in immuno-compromised patients, with mortality rates ranging from 60 to 90% (McNeil, M. M., S. L. Nash, R. A. Hajjeh, M. A. Phelan, L. A. Conn, B. D. Plikaytis, and D. L. Warnock. 2001. Trends in mortality due to invasive mycotic diseases in the United States, 1980-1997. Clin. Infect. Dis. 33:641-647), even following the recent introduction of new broad-spectrum antifungal agents. The most common species of *Aspergillus* causing invasive disease include *A. fumigatus*, *A. flavus*, *A. niger*, *A. terreus*, and *A. nidulans*. Other less common species can also cause the disease, but *A. fumigatus* accounts for ~90% of cases of IA (Denning, D. W. 1998. Invasive Aspergillosis. Clin. Infect. Dis. 26:781-805).

In the absence of a single 'gold standard' test for the disease, definitive diagnosis of IA encompasses data from clinical, radiological, serological, molecular biological, mycological and histopathological sources. It is imperative that diagnosis is made without delay, since prognosis worsens significantly in the absence of recognition and effective treatment. Rapid detection of IA using immuno-diagnostics has centred around the detection of fungal galactomannan (GM) (Latgé, J.-P., H. Kobayashi, J. P. Debeaupuis, M. Diaquin, J. Sarfati, J. M. Wieruszeski, E. Parra, J. P. Bouchara, and B. Fournet. 1994. Chemical and immunological characterization of the extracellular galactomannan secreted by *Aspergillus fumigatus*. Infect. Immun. 62:5424-5433, Pazos, C., J. Ponton, and A. Del Palacio. 2005. Contribution of (1→3)-β-D-glucan chromogenic assay to diagnosis and therapeutic monitoring of invasive aspergillosis in neutropenic adult patients: a comparison with serial screening for circulating galactomannan. J. Clin. Microbiol. 43:299-305, Quindos, G. 2006. New microbiological techniques for the diagnosis of invasive mycoses caused by filamentous fungi. Clin. Microbiol. Infect. 12:40-52). Monoclonal antibodies (mAbs) have been successfully used in the detection of GM, and they form the basis of commercial laboratory-based tests such as the Platelia *Aspergillus* ELISA kit that incorporates a rat mAb (EB-A2) directed against tetra (1→5)-β-D-galactofuranoside, the immunodominant epitope in the antigen (Morelle, W., M. Bernard, J.-P. Debeaupuis, M. Buitrago, M. Tabouret, and J.-P. Latgé. 2005. Galactomannoproteins of *Aspergillus fumigatus*. Euk. Cell 4:1308-1316, Stynen, D, A. Goris, J. Sarfati, and J.-P. Latgé. 1995. A new sensitive sandwich enzyme-linked immunosorbant assay to detect galactofuran in patients with invasive aspergillosis. J. Clin. Microbiol 33:497-500, Stynen, D., J. Sarfati, A. Goris, M.-E. Prevost, M. Lesourd, H. Kamphuis, V. Darras, and J.-P. Latgé. 1992. Rat monoclonal antibodies against *Aspergillus* galactomannan. Inf. Immun. 60:2237-2245). Immunoassays for GM detection mare a significant asset for managing patients at risk from IA because of detection of the antigen in the early stages of disease progression. Despite their widespread use, recent studies have revealed significant variation in performance. While specificity of the GM assay is consistently >85%, sensitivity of the assay can vary considerably between 29% and 100% and false-positive reactivity can vary from 5% in adults to 83% in newborn babies (Verweij, P. E., and M. A. S. H. Mennink-Kersten. 2006. Issues with galactomannan testing. Med. Mycol. 44:179-183). False positive results have been attributed to cross-reaction of mAb EB-A2 with GM from non-*Aspergillus* fungi (Giacchino, M., N. Chiapello, S. Bezzio, F. Fagioli, P. Saracco, A. Alfarano, V. Martini, G. Cimino, P. Martino, and C. Girmenia. 2006. *Aspergillus* galactomannan enzyme-linked immunosorbant assay cross-reactivity caused by invasive *Geotrichum capitatum*. J. Clin. Microbiol. 44:3432-3434, Kappe, R., and A. Schulze-Berge. 1993. New cause for false-positive results with the Pastorex *Aspergillus* antigen latex agglutination test. J. Clin. Microbiol. 31:2489-2490, Quindos, G. 2006. New microbiological techniques for the diagnosis of invasive mycoses caused by filamentous fungi. Clin. Microbiol. Infect. 12:40-52, Swanink, C. M. A., J. F. G. M. Meis, A. J. M. M. Rijs, J. P. Donnelly, and P. E. Verweij. 1997. Specificity of the sandwich enzyme-linked immunosorbant assay for detecting *Aspergillus* galactomannan. J. Clin. Microbiol. 35:257-260, Verweij, P. E., and M. A. S. H. Mennink-Kersten. 2006. Issues with galactomannan testing. Med. Mycol. 44:179-183), with galactoxylomannan from *Cryptococcus neoformans* (Dalle, F., P. E. Charles, K. Blanc, D. Caillot, P. Chavanet, F. Dromer, and A. Bonnin. 2005. *Cryptococcus neoformans* galactoxylomannan contains an epitope(s) that is cross-reactive with *Aspergillus* galactomannan. J. Clin. Microbiol. 43:2929-2931, De Jesus, M., E. Hackett, M. Durkin, P. Connolly, A. Casadevall, R. Petraitiene, T J. Walsh, and L J. Wheat. 2007. Galactoxylomannan does not exhibit cross-reactivity in the Platelia *Aspergillus* enzyme immunoassay. Clin. Vacc. Immun. 14:624-627), with lipoteichoic acid from intestinal bifidobacteria in the gastrointestinal microbiota of neonates (Mennink-Kersten, M. A. S. H., R. R. Klont, A. Warris, H. J. M. Op den Camp, and P. E. Verweij. 2004. Bifidobacterium lipoteichoic acid and false ELISA reactivity in *Aspergillus* antigen detection. Lancet 363:325-327), with the cancer prodrug cyclophosphamide (Hashiguchi, K., Y. Niki, and R. Soejima. 1994. Cyclophosphamide induces false-positive results in detection of *Aspergillus* antigen in urine. Chest 105:975-976), and with GM in food, drink and infant milk formulas (Ansorg, R., R. Van den Boom, and P. M. Rath. 1997. Detection of *Aspergillus* galactomannan antigen in foods and antibiotics. Mycoses 40:353-357). Contamination of β-lactam antibiotics with *Penicillium* GM may account for serum reactivity of patients receiving piperacillin/tazobactam or amoxicillin/clavulanic acid (Aubry, A., R. Porcher, J. Bottero, S. Touratier, T. Leblanc, B. Brethon, P. Rousselot, E. Raffoux, J.

Menotti, F. Derouin, P. Ribaud, and A. Sulahian. 2006. Occurrence and kinetics of false-positive *Aspergillus* galactomannan test results following treatment with β-lactam antibiotics in patients with hematological disorders. J. Clin. Microbiol. 44:389-394, Mattei, D., D. Rapezzi, N. Mordini, F. Cuda, C. Lo Nigro, M. Musso, A. Amelli, S. Cagnassi, and A. Gallamini. 2004 False-positive *Aspergillus* galactomannan enzyme-linked immunosorbant assay results in vivo during amoxicillin-clavulanic acid treatment. J. Clin. Microbiol. 42:5362-5363, Verweij, P. E., and M. A. S. H Mennink-Kersten. 2006. Issues with galactomannan testing. Med. Mycol. 44:179-183, Viscoli, C. M. Macherri, P. Cappellano, B. Bucci, P. Bruzzi, M. T. Van Lint, and A. Bacigalupo. 2004. False-positive galactomannan Platelia *Aspergillus* test results for patients receiving piperacillin-tazobactam. Clin. Infect. Dis. 38:913-916), although these reports have been disputed (Wu, D. H. 2004. Platelia *Aspergillus* assay and potential cross-reaction. Clin. Infect. Dis. 39:1402). There is therefore scope in IA immuno-diagnostics for tests that employ mAbs directed at epitopes other than those present on GM. While a 'pan-fungal' test that detects fungal (1→3)-β-D-glucan has been used for the diagnosis of invasive fungal infections (Pazos, C., J. Ponton, and A. Del Palacio. 2005. Contribution of (1→3)-β-D-glucan chromogenic assay to diagnosis and therapeutic monitoring of invasive aspergillosis in neutropenic adult patients: a comparison with serial screening for circulating galactomannan. J. Clin. Microbiol. 43:299-305, Quindos, G. 2006. New microbiological techniques for the diagnosis of invasive mycoses caused by filamentous fungi. Clin. Microbiol. Infect. 12:40-52) its lack of specificity means that it is unable to discriminate between *Aspergillus* species and other opportunistic pathogens, which compromises the ability to select the most appropriate antifungal agent. In contrast, an ELISA used to detect the Afmp1p cell wall antigen of *A. fumigatus* in patient's sera provides a high degree of specificity but does not allow the detection of IA caused by other *Aspergillus* species (Woo, P. C. Y., C-M. Chan, A. S. P. Leung, S. K. P. Lau, X-Y Che, S. S. Y. Wong, L. Cao, and K-Y. Yuen. 2002. Detection of cell wall galactomannoprotein Afmp1p in culture supernatants of *Aspergillus fumigatus* and in sera of aspergillosis patients. J. Clin. Microbiol. 40:43824387). Furthermore, combinations of antibody and antigen testing of serum samples are required to provide serodiagnostic sensitivities for *A. fumigatus* IA detection comparable to GM tests.

Development of a non-invasive immunodiagnostic test that is rapid, reliable and relatively inexpensive and that detects surrogate (non-GM and non-Afmp1p) markers for IA, would allow routine testing of vulnerable patients who have an elevated risk of infection, such as allogeneic haematopoietic stem-cell-transplant recipients, patients with haematological malignancies and recipients of solid organ transplants, especially of the lung. The inventors here report the development of a mouse hybridoma cell line secreting an *Aspergillus* glycoprotein-specific mAb (JF5) and its utilization in the development of a lateral flow device (LFD) for the rapid serodiagnosis of IA. The assay exploits lateral flow technology that has been used, to date, in diagnostic tests for viruses, bacteria and toxins (Iweala, O. I. 2004. HIV diagnostic tests: an overview. Contraception 70:141-147, Ketema, F., C. Zeh, D. C. Edelman, R. Saville, and N. T. Constantine. 2001. Assessment of the performance of a rapid, lateral flow assay for the detection of antibodies to HIV. J. Acquir. Immune. Defic. Syndr. 27:63-70, Sharma, S. K., B. S. Eblen, R. L. Bull, D. H. Burr, and R. C. Whiting. 2005. Evaluation of lateral-flow *Clostridium botulinum* neurotoxin detection kits for food analysis. Appl. Environ. Microbiol. 71:3935-3941, Shyu, R. H., H. F. Shyu, H. W. Liu, and S. S. Tang. 2002. Colloidal gold-based immunochromatographic assay for detection of ricin. Toxicon 40:255-258, Smits, H. L., C. K. Eapen, S. Sugathan, M. Kuriakose, M. H. Gasem, C. Yersin, D. Sasaki, B. Pujianto, M. Vestering, T. H. Abdoel, and G. C. Gussenhoven. 2001. Lateral-flow assay for rapid serodiagnosis of human leptospirosis. Clin. Diagn. Lab. Immunol. 8:66-169) and, most famously, for the home pregnancy tests first introduced by Unipath in 1988. While immunochromatographic assays have been developed for the identification of *Candida* species (Marot-Leblond, A., L. Grimaud, S. David, D. J. Sullivan, D. C. Coleman, J. Ponton, and R. Robert. 2004. Evaluation of a rapid immunochromatographic assay for identification of *Candida albicans* and *Candida dubliniensis*. J. Clin. Microbiol. 42:4956-4960) and for the detection of fungi in soil (Thornton, C. R. Tracking fungi in soil with monoclonal antibodies. Eur. J. Pl. Pathol. 121:347-353, Thornton, C. R., A. C. Groenhof, R. Forrest, and R. Lamotte. 2004. A one-step, immunochromatographic lateral flow device specific to *Rhizoctonia solani* and certain related species, and its use to detect and quantify *R. solani* in soil Phytopathol. 94:280-288) this is the first time, to the best of the inventor's knowledge, that an LFD has been developed for the detection of *Aspergillus* antigens in human serum.

Current diagnostic tests for IA are confined to laboratories equipped to perform GM, β-glucan or nucleic acid-based diagnostic tests. The simplicity of the LFD format allows it to be used with minimal training and provides an additional diagnostic platform for the management of IA in high-risk patient groups. The ability of the LFD to detect *Aspergillus* antigens in clinical samples is demonstrated using sera from IA patients. Furthermore, its superior sensitivity in detecting IA compared to current galactomannan and β-glucan tests is shown using sera from a guinea pig model of disease.

SUMMARY OF THE INVENTION

In order to provide a new diagnostic tool for use in diagnosing *Aspergillus* antigens, the inventors identified an *Aspergillus* antigen found in growing hyphae. The inventors then produced molecules that bind to that antigen. The particular binding molecules, especially antibodies, may be used to not only identify an *Aspergillus* infection, but also to distinguish between active, growing colonies of *Aspergillus* and quiescent or dead colonies.

According to a first aspect of the invention, there is provided a hybridoma deposited under accession number ECACC 08120202.

According to a second aspect of the invention, there is provided an antibody which may be obtained by culture of the hybridoma, or a functional fragment of such an antibody.

According to a third aspect of the invention, there is provided an antibody, or antibody fragment or other molecule capable of specifically binding to *Aspergillus*, that antibody, fragment or binding molecule comprising a CDR, light chain, heavy chain, light chain variable region, heavy chain variable region or antigen binding region, especially FAb region, that shows substantial homology with the corresponding region of the antibody according to the second aspect of the invention. Preferably, the antibody, fragment or binding molecule also exhibits similar binding properties to the antibody according to the second aspect of the invention.

According to a fourth aspect, there is provided an antibody comprising a CDR comprising an amino acid sequence having substantial homology to an amino acid sequence selected from the sequences shown in FIGS. 19 to 25.

In particular, there is provided an antibody comprising a first CDR comprising an amino acid sequence having substantial homology to the amino acid sequence shown in FIG. 19;
a second CDR comprising an amino acid sequence having substantial homology to an amino acid sequence selected from the sequences shown in FIGS. 21 or 22; and
a third CDR comprising an amino acid sequence having substantial homology to the amino acid sequence shown in FIG. 24.

In particular, there is provided an antibody comprising a first CDR comprising an amino acid sequence having substantial homology to the amino acid sequence shown in FIG. 20;
a second CDR comprising an amino acid sequence having substantial homology to the amino acid sequence shown in FIG. 23; and
a third CDR comprising an amino acid sequence having substantial homology to the amino acid sequence shown in FIG. 25.

Also provided is an antibody comprising a heavy chain comprising one or more CDRs having an amino acid sequence having substantial homology to an amino acid sequence selected from the sequences shown in FIGS. 19, 21, 22 and 24.

The invention further provides an antibody comprising a light chain comprising one or more CDRs having an amino acid sequence having substantial homology to an amino acid sequence selected from the sequences shown in FIGS. 20, 23 and 25.

Additionally, there is provided an antibody comprising an amino acid sequence having substantial homology to an amino acid sequence selected from the sequences shown in FIGS. 2, 4, 6, 8, 10, 11, 13, 15, 17 and 18.

The invention also provides an antibody comprising a heavy chain variable region having substantial homology to an amino acid sequence selected from the sequences shown in FIGS. 2, 4, 6, 8, 10 and 11.

Preferably the antibody has a light chain variable region having substantial homology to the amino acid sequence selected from the sequences shown in FIGS. 13, 15, 17 and 18.

In the amino acid sequences X is any amino acid. Preferably it is a non-polar amino acid, especially glycine. n is an integer between 0 and 8, preferably between 0 and 5, more preferably between 0 and 3, more preferably between 0 and 2, more preferably 0. Where a sequence contains more than one X, for example where n is greater than one, X may represent the same or a number of different amino acids. Where a sequence contains more than one $X_n$, each X may represent the same or a number of different amino acids. Each n may represent the same or different integers.

The invention further provides an antibody encoded by a nucleotide sequence having substantial homology to a nucleotide sequence selected from the sequences shown in FIGS. 1, 3, 5, 7, 9, 12, 14 and 16.

Also provided is an antibody comprising a heavy chain variable region encoded by a nucleotide sequence having substantial homology to a nucleotide sequence selected from the sequences shown in FIGS. 1, 3, 5, 7 and 9.

Preferably the antibody comprises a light chain variable region encoded by a nucleotide sequence having substantial homology to the nucleotide sequence selected from the sequences shown in FIGS. 12, 14 and 16.

In another embodiment, there is provided an antibody that binds to the same epitope as an antibody according to other aspects of the invention.

In order that the invention may be better understood, certain terms are defined. Additional definitions may be found throughout the specification.

The term "antibody" is well known in the art. Herein it means an immunoglobulin or any functional fragment thereof. It encompasses any polypeptide that has an antigen-binding site. It includes but is not limited to monoclonal, polyclonal, monospecific, polyspecific, non-specific, humanized, human, single-chain, chimeric, synthetic, recombinant, hybrid, mutated, grafted, and in vitro generated antibodies. The term "antibody" encompasses antibody fragments such as Fab, F(ab') 2, Fv, scFv, Fd, dAb, and any other antibody fragments that retain antigen-binding function. Typically, such fragments would comprise an antigen-binding domain. When preceded by the word "intact" the term "antibody" means a whole antibody molecule, namely two heavy chains, each with one variable region and three constant regions, and two light chains, each with one variable region and one constant region.

Intact antibodies are also known as immunoglobulins (Ig). As indicated above, intact antibodies comprise light chains and heavy chains. Light chains are classified into two isotypes, and heavy chains are classified into five isotypes (A, D, E, G, and M). Some heavy chain isotypes are further divided into isotype subclasses, e. g., IgG1, IgG2, IgG3, and IgG4. It is particularly preferred, that the antibodies of the invention are IgG antibodies. In particular, IgG2b and IgG2a antibodies are preferred.

The domain and three dimensional structures of different antibodies are known in the art. The light chain is composed of a constant domain (C) and an N-terminal variable domain (V). The heavy chain is composed of three or four constant domains ($C_H$), a hinge region, and a N-terminal variable domain ($V_H$). The $C_H$ adjacent to the $V_H$ domain is designated $C_{H1}$. The $V_H$ and $V_L$ domains contain four regions of conserved sequence called framework (FR) regions (FR1, FR2, FR3, and FR4), which form a scaffold for three regions of hypervariable sequence called complementarity determining regions (CDR). The CDRs (CDR1, CDR2, and CDR3) contain most of the antibody amino acids that specifically binds antigen. Heavy chain CDRs are denoted H1, H2, and H3, while light chain CDRs are denoted L1, L2, and L3. The term CDR is well known in the art. One skilled in the art would be able to recognise CDRs in an antibody or fragment by using Kabat numbering and the amino acids found either side of the CDRs.

The Fab fragment (Fragment antigen-binding) consists of $V_H$, $C_{H1}$, $V_L$ and $C_L$ domains covalently linked by a disulfide bond between the constant regions. The Fv fragment is smaller and consists of $V_H$ and $V_L$ domains non-covalently linked. To overcome the tendency of non-covalently domains to dissociate, a single chain Fv fragment (scFv) can be constructed. The scFv contains a flexible polypeptide that links the C-terminus of $V_H$ to the N-terminus of $V_L$, or the C-terminus of $V_L$ to the N-terminus of $V_H$. A 15-mer $(Gly_4Ser)_3$ peptide may be used as a linker, but other linkers are well known.

The terms "antigen-binding site", "antigen-binding domain" and "antigen-binding fragment" mean the part of an antibody that specifically binds antigen. The part of the antigen that is recognised and bound by the antibody is referred to as the "epitope". An antigen-binding domain usually comprises variable regions from both the light chain ($V_L$) and the heavy chain ($V_H$), but it does not have to comprise both. Antigen-binding fragments include Fab fragments (monovalent fragments consisting of the $V_L$, $V_H$, $C_L$ and $C_{H1}$ domains): F(ab')$_2$ fragments (bivalent fragments comprising two Fab fragments linked by a disulfide bridge at the hinge region); Fd fragments (the two $V_H$ and $C_{H1}$ domains); Fv fragments ($V_L$ or $V_H$ domains, dAb fragments (Ward et al., (1989) Nature 341: 544-546), one or more complementarity determining regions (CDR); and single chain Fvs. The various antibody fragments can be obtained using conventional techniques known to those with skill in the art. It is possible to screen for the functionality of the fragments, e.g. binding and agonising a receptor using techniques known in the art.

As is known in the art, it is possible to use murine antibodies from mice and rats for therapy in humans. However, rodent antibodies tend to provoke strong Human anti-Murine Antibody (HAMA) immune responses which restricts their usefulness for repeated application in the same patient. Hence, the antibodies according to the invention are preferably chimeric, humanised (CDR grafted or reshaped).

The term "chimeric" refers to antibodies in which the whole of the variable regions of a mouse or rat antibody are expressed along with human constant regions. This provides the antibody with human effector functions and also reduces immunogenicity (HAMA) caused by the murine Fc region.

"Humanised" antibodies (also called CDR grafted or "reshaped antibodies") are an alternative to chimeric antibodies in which only the complementarity determining regions from the rodent antibody V-regions are combined with framework regions from human V-regions. The idea is that these antibodies should be more human-like than chimeric and thus perhaps less immunogenic than chimeric antibodies.

It is also possible to obtain fully human antibodies from transgenic mice or other transgenic animals. Transgenic mice have been created which have a repertoire of human immunoglobulin germline gene segments. These mice when immunised thus make human like antibodies. B cells from such immunised mice may be used in the production of monoclonal antibodies.

All of these types of antibodies are encompassed by the invention.

As mentioned above, the invention also encompasses functional fragments of antibodies. Whilst certain fragments are mentioned specifically, any functional fragment, that is to say, any fragment that exhibits similar binding properties as the relevant whole antibody is encompassed by the invention.

The antibodies of the invention are preferably able to bind to an epitope from an *Aspergillus* cell, especially an *Aspergillus fumigatus* cell. It is particularly preferred that the epitope is from growing hyphae. The antibodies and nucleic acids of the invention are preferably isolated. The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% (w/w) pure; or at least 95%, 96%, 97%, 98%, 99%, or 100% (w/w) pure.

The phrase "substantially homologous" means that the relevant amino acid or nucleotide sequence (e. g., CDR (s), $V_H$ or $V_L$ domain) will be identical to or have minor differences to the specifically defined sequences. Minor differences include minor amino acid changes, such as 1 or 2 substitutions in a 5 amino acid sequence of a specified region. In the case of antibodies, the second antibody has the same specificity and has at least 50% of the affinity of the same.

Sequences substantially identical or homologous (e. g., at least about 85% sequence identity) to the sequences disclosed herein are also part of this application. In some embodiments, the sequence identity can be about 90%, 91%, 92%, 93%, 94%, 95%, 96%, 97%, 98% or 99% or higher. In particular, when dealing with sequences of CDRs, substantial homology preferably means at least 90%, 91%, 92%, 93%, 94%, 95%, 96%, 97%, 98%, 99% homology. When dealing with longer sequences, such as the sequences of the light or heavy chain variable regions, homology may be at least 85%, 87%, 90%, 91%, 92%, 93%, 94%, 95%, 96%, 97%, 98% or 99%. Sequences including constant regions may have less homology, for example, 75%, 80%, 85%, 87%, 90%, 91%, 92%, 93%, 94%, 95%, 96%, 97%, 98% or 99% or higher. Substantially identical or homologous sequences also include nucleic acid sequences that will hybridize under selective hybridization conditions (e. g., highly stringent hybridization conditions), to the complement of the specifically defined strand. The percent identity can be determined by standard alignment algorithms, for example, the Basic Local Alignment Tool (BLAST) described by Altshul et al. ((1990) J. Mol. Biol., 215: 403410); the algorithm of Needhsul at al. ((1970) J. Mol. Biol., 48: 444-453); or the algorithm of Meyers et al. ((1988) Comput. Appl. Biosci., 4: 11-17). The percent identity between two amino acid or nucleotide sequences can also be determined using the algorithm of E. Meyers and W. Miller ((1989) CABIOS, 4: 11-17) which has been incorporated into the ALIGN program (version 2.0). This would be known by those skilled in the art.

The term "stringent" describes conditions for hybridization and washing. Stringent conditions are known to those skilled in the art and can be found in Current Protocols in Molecular Biology, John Wiley & Sons, N.Y. (1989), 6.3.1-6.3.6.

Antibodies can be made by any method known in the art. A preferred method is using traditional hybridoma techniques (Kohler and Milstein (1975) Nature, 256: 495-499). For additional antibody production techniques, see Antibodies: A Laboratory Manual, eds. Harlow a al., Cold Spring Harbor Laboratory, 1988. No limitation is placed on the present invention as to method of production or source of antibody.

The invention provides antibodies that bind to *Aspergillus*. It is further envisaged that one skilled in the art could create more antibodies by altering the V, and/or $V_L$ sequence(s) provided. Such antibodies may be derived by a skilled person using techniques known in the art and are also encompassed by the invention. For example, modifications such as amino acid substitutions, deletions, or additions can be introduced into any part of the antibody, providing functionality remains. Changes may be introduced into the framework regions, especially to, for example improve the stability of the antibody. Changes may also be introduced into the CDRs to alter the antibody's affinity for the epitope. The affinity of an antibody for the epitope may be tested using standard techniques known in the art.

Conservative modifications to the $V_H$ and $V_L$ sequences are envisaged in particular. Such changes will produce molecules having functional and chemical characteristics similar to those of the antibodies from which the modifications are made. Conservative modifications are modifications unlikely to dramatically change the shape or function of the antibody, such as replacing one amino acid with another amino acid that has similar characteristics, e.g. replacing a hydrophobic amino acid with another hydrophobic amino acid.

When substituting amino acids, natural amino acids may be used, as may non-naturally occurring amino acids that have been created by, for example, chemical synthesis.

The antibodies according to the invention may be linked to other molecules. For example, antibodies may be linked to a protein or to a nonproteinaceous polymer such as polyethylene glycol, polypropylene glycol, and polyoxyalkylenes. Linking antibodies to such molecules is well known in the art and may be carried out by standard methods. Linking antibodies to such molecules can have an effect on certain characteristics of the antibodies, for example half life in blood.

Other molecules that may be linked to the antibody include detectable or functional tags or labels, such as enzymatic labels, e.g. horseradish peroxidase or alkaline phosphatase, radiolabels and chemical moieties e.g. biotin. The antibodies may also be linked to toxic agents such as toxins, cytostatic or cytotoxic molecules and radioisotopes. Alternatively, the antibodies may be linked to other antibodies.

The invention also provides methods of making antibodies, including a method of generating an antibody or functional fragment thereof comprising:
a) providing a repertoire of nucleic acids encoding a variable domain that either includes a CDR1, CDR2 or CDR3 encoding region to be replaced or lacks a CDR1, CDR2 or CDR3 encoding region;
b) combining the repertoire with a donor nucleic acid having a nucleotide sequence encoding a sequence selected from the sequences in FIGS. 19 to 25 to provide a repertoire of nucleic acids encoding a variable domain; and
c) expressing a nucleic acid from the repertoire.

When replacing or inserting a nucleotide sequence encoding a CDR, one skilled in the art would use standard techniques and would know whether the CDR sequence could be inserted in isolation or whether framework regions should also be inserted. The skilled person would be able to make appropriate changes to the framework region if necessary.

The term "repertoire" refers to a genetically diverse collection of nucleotide sequences derived wholly or partially from sequences encoding immunoglobulins. The sequences may be generated by the method given above, or by rearrangement in vivo of the V, D, and J segments of heavy chains, and the V and J segments of light chains. Alternatively, the sequences can be generated from a cell in response to which rearrangement occurs, e. g., in vitro stimulation. Alternatively, part or all of the sequences may be obtained by DNA splicing, nucleotide synthesis, mutagenesis, and other methods, see, e. g., U.S. Pat. No. 5,565, 332.

The method may additionally comprise selecting an antibody that binds an *Aspergillus* epitope from the expressed antibodies and isolating it.

The invention also provides isolated nucleic acids encoding antibodies according to the invention including nucleotides encoding the CDRs, variable domains and other functional fragments of such antibodies, and substantially homologous sequences. The nucleic acids may comprise DNA or RNA, and they may be synthetic (completely or partially) or recombinant (completely or partially).

The nucleotide sequences provided and references thereto encompass DNA molecules with the specified sequence, and encompass RNA molecules with the specified sequence in which U is substituted for T.

A nucleic acid may encode any part of the antibody for example, a CDR, a variable region, a light chain, a heavy chain, an scFv, a Fab, the entire antibody or any other functional fragment thereof.

Particularly provided is an isolated nucleic acid having substantial homology to a sequence selected from the sequences shown in FIGS. 1, 3, 5, 7, 9, 12, 14 and 16.

The nucleic acids of the invention are substantially homologous to the sequences provided. In particular, the sequences are preferably at least 85%, 90%. 91%, 92%, 93%, 94%, 95%, 96%, 97%, 98%, 99% homologous to the sequences provided.

The invention also provides constructs such as plasmids, vectors, transcription or expression cassettes, which comprise at least one nucleic acid according to the invention.

Also provided is a host cell comprising at least one such construct.

Further provided is a method of making an antibody comprising culturing host cells under appropriate conditions so they express the antibody from the nucleic acid. Following expression and production, any desired fragment or antibody may be isolated and/or purified using any suitable technique, then used as appropriate.

Systems for cloning and expressing polypeptides in a variety of host cells are known in the art. Suitable host cells include mammalian cells, insect cells, plant cells, yeast cells, or prokaryotic cells, e.g., *E. coli*. Mammalian cells available in the art for heterologous polypeptide expression include lymphocytic cell lines (e. g., NSO), HEK293 cells, Chinese Hamster Ovary (CHO) cells, COS cells, HeLa cells, baby hamster kidney cells, oocyte cells.

It is particularly preferred that the antibodies of the invention are monoclonal antibodies. Monoclonal antibodies may be produced by standard methods, as first described by Kohler and Milstein.

The antibodies may be produced using a hybridoma. A hybridoma is well known in the art, is a cell created artificially by fusion of a tumour cell with a B-lymphocyte. Such cells are produced in the standard method of producing monoclonal antibodies, as first described by Kohler and Milstein.

The antibodies of the invention have multiple uses. Firstly, they may be used to identify the presence of an *Aspergillus* species, especially *Aspergillus fumigatus*. This may be a diagnostic use, identifying the presence of the species in a sample obtained from a patient. Also the use may be to identify the presence of the species in a sample obtained from a location, such as a building where an *Aspergillus* species may be present. The sample may be a swab taken from a wall of such a building, for example.

Also provided is a method of assaying for the presence of an *Aspergillus* species in a sample, comprising:
a) contacting the sample with labeled antibodies according to the invention; and b) observing the sample for binding of the antibodies to epitopes in the sample;
wherein binding of the antibodies is indicative of the presence of an *Aspergillus* species.

The sample may be a sample obtained from a human or animal, and may be any appropriate sample, for example blood, serum, urine, plasma or bronchioalveolar lavage (BAL). Alternatively, the sample may be obtained from a site thought to contain *Aspergillus*, for example a swab taken from a building wall.

A labeled antibody is an antibody to which a detectable label has been attached. Suitable labels are well known in the art and examples are discussed above.

Also provided is a device or kit for carrying out the assay method, comprising a labeled antibody according to the invention. Preferably the device or kit is in the form of a lateral flow device.

There is provided a pharmaceutical composition comprising an antibody according to the invention.

The composition is suitable for administration to patients. In addition to the antibody, it may comprise one or more appropriate pharmaceutical excipient(s) such as solvents, dispersion media, coatings, antibacterial and antifungal agents, isotonic and absorption delaying agents. The preparation of pharmaceutical compositions and the use of excipients is well known in the art. Other active compounds may also be included. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. It may be possible to create compositions which may be topically or orally administered, or which may be capable of transmission across mucous membranes. For example, the administration may be intravenous, intraperitoneal, intramuscular, intracavity, subcutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, CREMOPHOR® ELT (BASF, Parsippany, N.J.) (polyethoxylated castor oil), ethanol, or polyol. In all cases, the composition must be sterile and fluid for easy syringability. Proper fluidity can often be obtained using lecithin or surfactants. The composition must also be stable under the conditions of manufacture and storage Prevention of microorganisms can be achieved with antibacterial and antifungal agents, e. g. , parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e. g. , aluminium monostearate and gelatin.

Oral compositions include an inert diluent or edible carrier. The composition can be enclosed in gelatin or compressed into tablets. For the purpose of oral administration, the antibodies can be incorporated with excipients and prepared as tablets or capsules, for example. The oral composition may also contain, for example, a binder, an excipient, a lubricant and flavourings.

Compositions may also be administered by a transmucosal or transdermal route. For example, antibodies that comprise a Fc portion may be capable of crossing mucous membranes in the intestine, mouth, or lungs (via Fc receptors). Transmucosal administration can be accomplished through the use of lozenges, nasal sprays, inhalers, or suppositories. Transdermal administration can also be accomplished through the use of composition containing ointments, salves, gels, or creams known in the art. For transmucosal or transdermal administration, penetrants appropriate to the barrier to be permeated are used.

For administration by inhalation, antibodies are delivered in an aerosol spray from a pressured container or dispenser, which contains a propellant (e. g., liquid or gas) or a nebulizer.

In certain embodiments, antibodies of this invention are prepared with carriers to protect the antibodies against rapid elimination from the body. Biodegradable polymers (e. g., ethylene vinyl acetate, polyanhydrides, polyglycolic acid, collagen, polyorthoesters, polylactic acid) are often used.

Methods for the preparation of such pharmaceutical compositions are known by those skilled in the art.

Antibodies or compositions according to the invention may be administered in therapeutically effective amounts, as determined, based on, for example, the patient's weight, gender, age and medical condition. The antibodies or compositions may be administered in a single dose, as a bolus or as continuous therapy.

The term effective amount refers to an amount sufficient to provide a therapeutic or diagnostic effect.

The term "non-human animals" of the invention includes all vertebrates, such as non-human primates, sheep, dogs, cows, chickens, amphibians, reptiles, etc.

Additionally, there is provided an antibody or functional fragment thereof according to the invention for use in therapy. The antibody or fragment is especially for use in the treatment of an infection with an *Aspergillus* species.

Also provided is a method of treating an infection with an an *Aspergillus* species, comprising administering a therapeutic amount of an antibody or fragment thereof according to the invention to a subject in need thereof.

BRIEF DESCRIPTION OF THE DRAWINGS

FIGS. 1 to 25 show amino acid sequences and nucleotide sequences of antibodies and fragments thereof according to the invention. FIGS. 1 to 25 disclose SEQ ID NOS 1-25, respectively, in order of appearance.

A. Western immunoblot with monoclonal antibody (mAb) JF5 after separation of purified antigen by SDS-PAGE under reducing conditions. Well was loaded with 0.2 μg of protein.

B. Western immunoblot with mAb JF5 after treatment of purified antigen with peptide-N-glycosidase and separation by SDS-PAGE under denaturing conditions. Well was loaded with 0.2 μg of protein.

Figure 27:
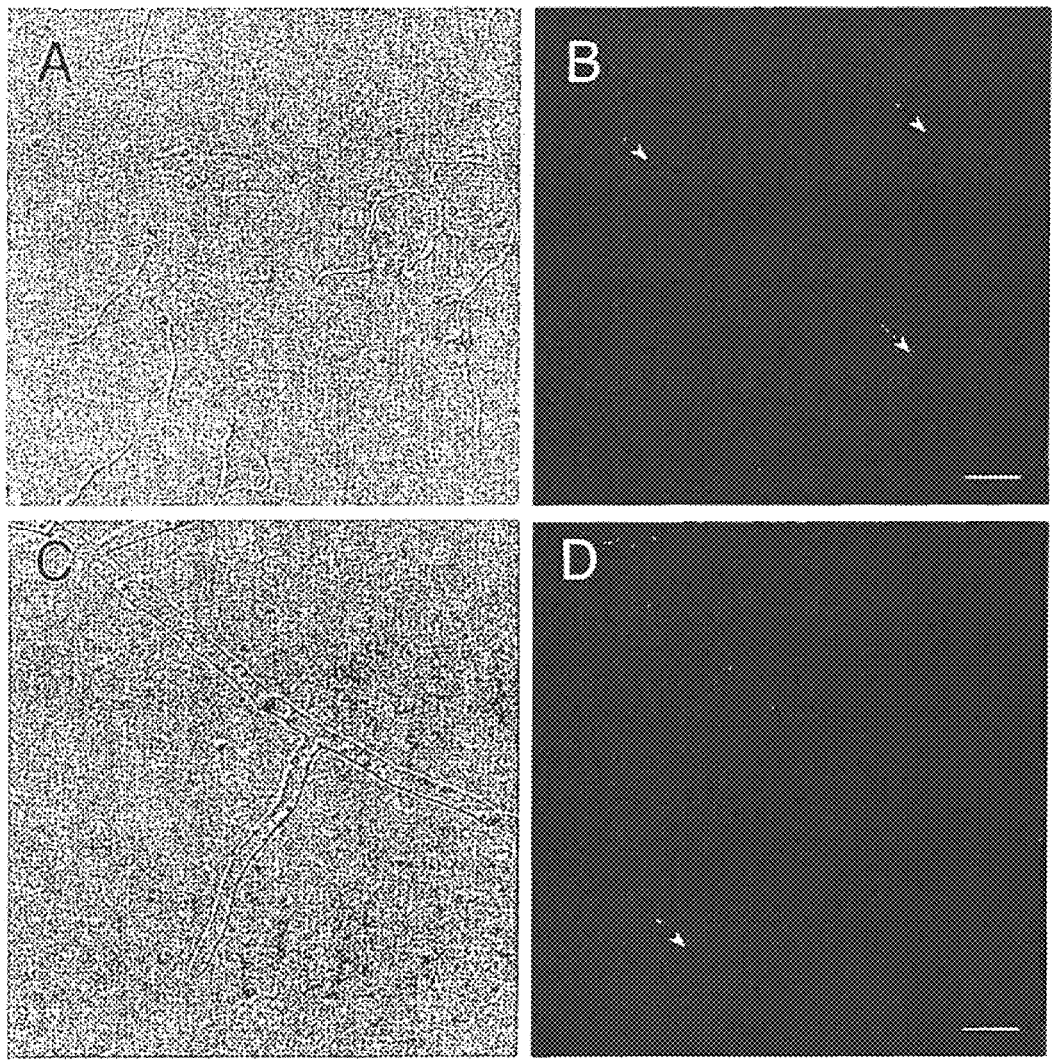

FIG. 27. Photomicrographs of *A. fumigatus* AF293 cells immuno-stained with JF5 and anti-mouse polyvalent immunoglobulin FITC.

A. Germlings examined under bright-field microscopy

B. Same slide as in (A), but examined under epifluorescence. Note intense staining of the cell walls of germ tubes, but lack of staining in ungerminated conidia (arrowed)

C. Hypha examined under bright-field microscopy

D. Same slide as in (C), but examined under epifluorescence. Note intense staining of cell wall and secretion of the antigen at the growing tip (arrowed). Bar, 6 μm.

Figure 28:
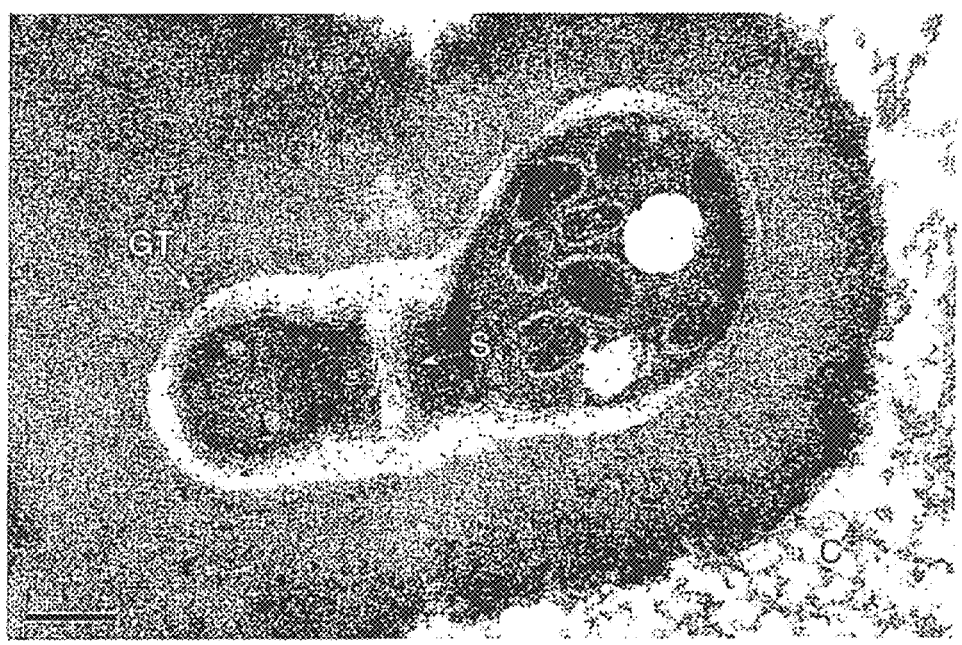

FIG. 28. Immunogold localization of JF5 antigen in cells of *A. fumigatus* AF293. Longitudinal section of germling grown in human serum, showing localization of antigen in the cell walls of the germ tube (GT) and swollen conidium, in the septum (S), and in a surrounding capsular-like layer (C). Bar, 0.5 µm.

Figure 29:
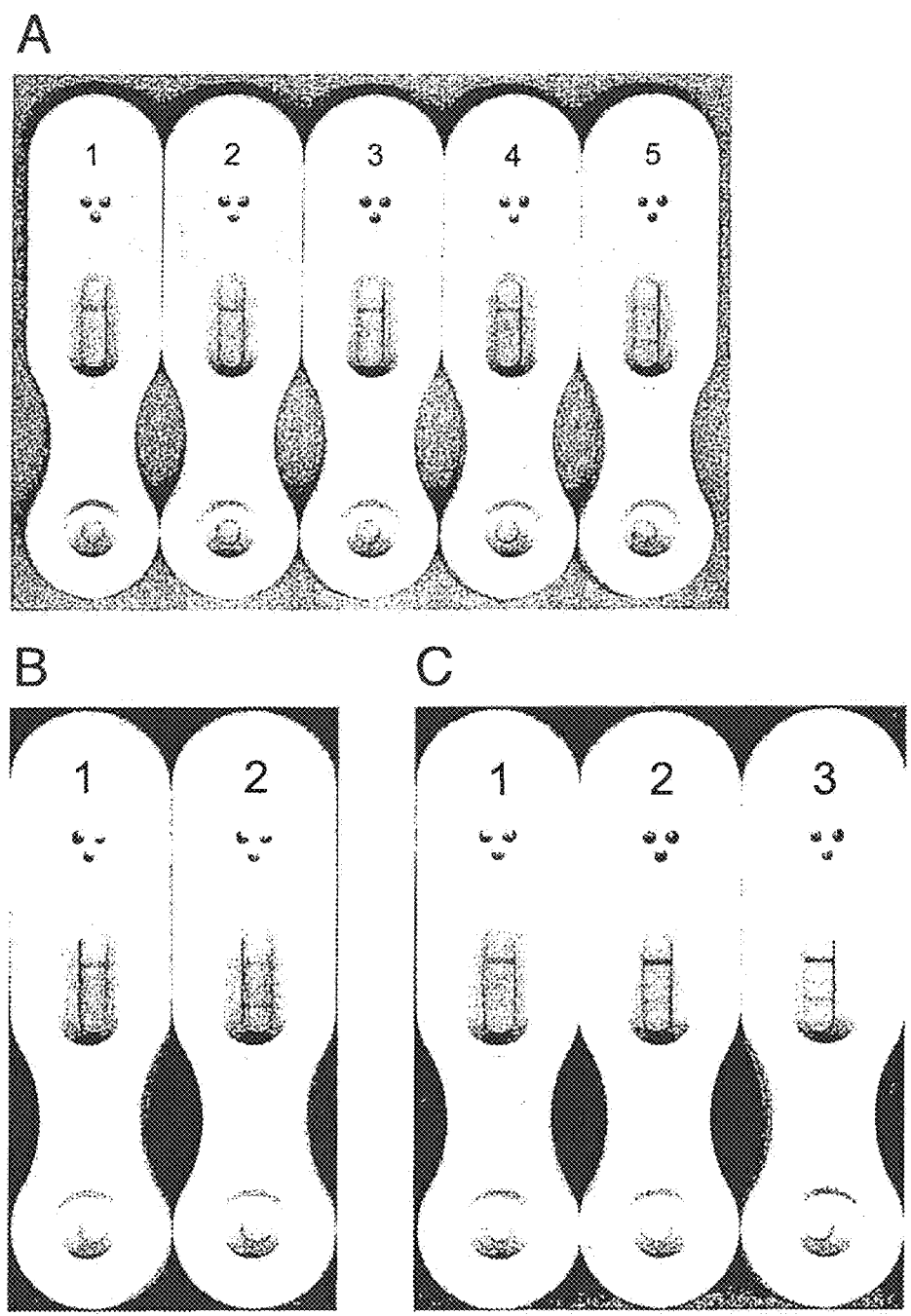

FIG. 29. Serum LFD tests.

A. LFD tests with normal human serum following inoculation with fungi and incubation for 48 h at 37° C. Negative reactions (single control line only) exhibited by *Candida albicans* (1), *Pseudallescheria boydii* (2), *Rhizopus oryzae* (3), *Fusarium solani* (4) and positive reaction (two lines) with *Aspergillus fumigatus* (5) are shown.

B. LFD tests of normal human serum (1), and serum spiked with affinity purified antigen (2) at a concentration of 2.5 µg protein/m).

C. Examples of results from LFD tests of serum samples from healthy individuals or patients confirmed with IA. Negative, weak and strong reactions exhibited with specimen numbers 9OHD (I), 1657 (2), and 1131 (3) are shown. Specimen numbers relate to those shown in Table 4.

Figure 30:
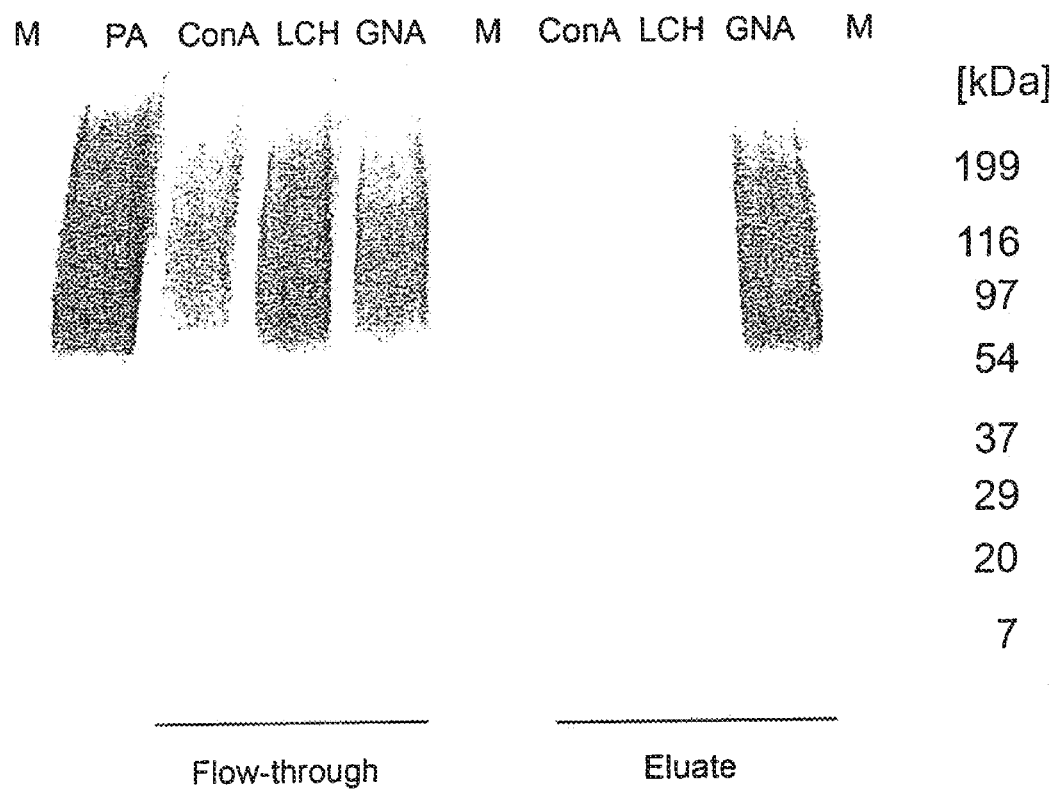

FIG. 30. Analysis of flow-through and eluate fractions from lectin spin columns by using denaturing SDS-PAGE and Western blotting. Lanes M, molecular mass markers; lane PA, untreated purified antigen; lanes LCH, ConA and GNA, flow-through or eluate fractions from lentil lectin (*Lens culinaris* hemagglutinin), Concanavalin A lectin or snowdrop lectin (*Galanathus nivalis* agglutinin) spin columns respectively. All wells were loaded with 0.5 µg of protein. Note strong binding of MAb JF5 to eluate fraction from GNA spin column showing that the JF5 glycoprotein antigen(s) comprises terminal non-reducing mannose residues linked α1-3 and α1-6.

Figure 31:
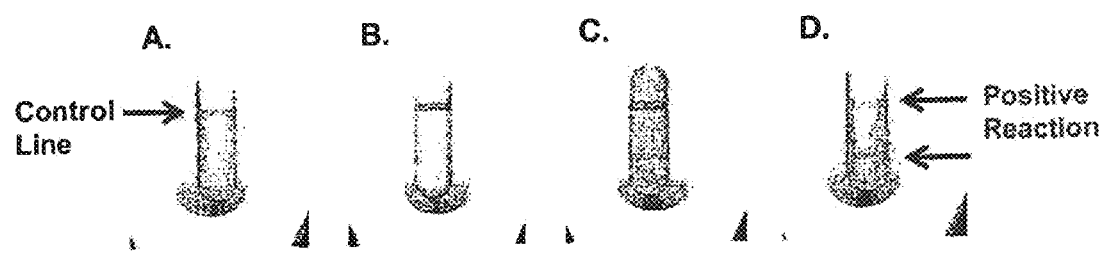

FIG. 31. Examples of results from (A) negative, (B) weakly positive, (C) moderately positive, and (D) strongly positive lateral-flow device assays. In the absence of the *Aspergillus* antigen, no complex was formed in the zone containing solid-phase JF5 antibody, and a single internal control line was observed (A).

Figure 32:
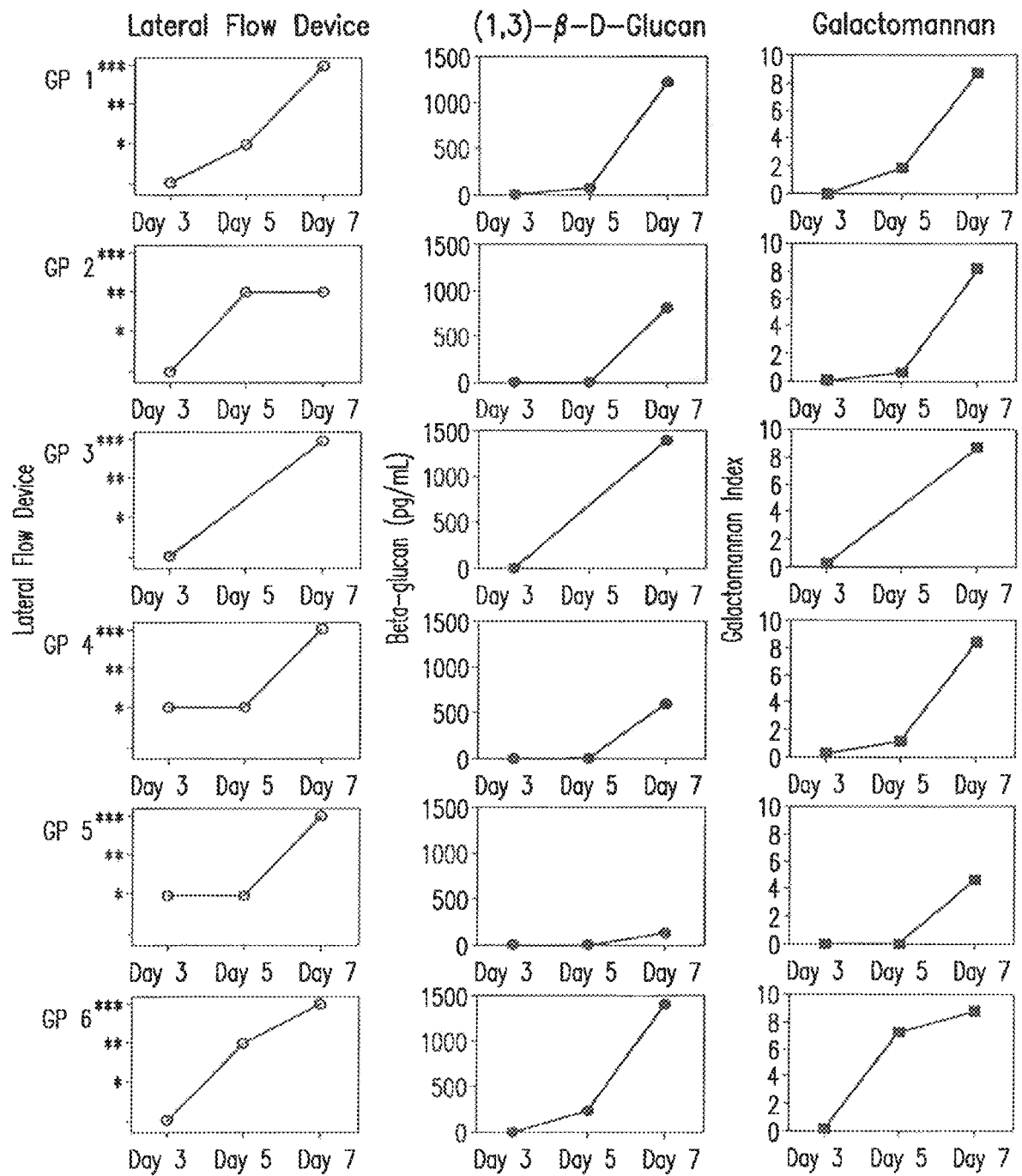

FIG. 32. Results from serial serum samples collected over time from the same guinea pigs with invasive pulmonary aspergillosis as measured by lateral-flow technology (A), the galactomannan assay (B), and the (1→3)-β-D-glucan assay (C). Each line represents the biomarker results from one animal at multiple time points. Serial samples were available for measurement of each biomarker at the multiple time points in 6 guinea pigs. For the y-axis of the lateral-flow device graph (A), + represents weakly positive results, ++ moderately positive results, and +++ strongly positive results.

DETAILED DISCLOSURE

Example 1

Fungal Culture.

All fungi were cultured on Sabouraud agar (SA) under a 16 h fluorescent light regime.

Development of mAb, Preparation of Immunogen, and Immunization Regime.

Mice were immunized with lyophilized mycelium (LM) of *A. fumigatus* AF293. Minimal medium (19 mM $(NH_4)_2PO_4$, 0.5% (wt/vol) yeast extract, 7 mM sodium citrate, 2 mM $MgSO_4 \cdot 7H_2O$, 0.5 mM $CaCl_2H_2O$ and 50 mM glucose, adjusted to pH 5.5 with 1 N HCl) was sterilized by autoclaving at 121° C. for 15 min. Three-wk-old SA Petri dish cultures of the fungus were flooded with 20 ml $dH_2O$ and the conidia suspended by gentle agitation using an inoculation loop. Spore suspensions were filtered through Miracloth to remove mycelium and the filtrate containing conidia transferred to 1.5 ml micro-centrifuge tubes. The conidia were washed three times with $dH_2O$ by repeated vortexing and centrifugation at 12 000 g for 5 min and finally suspended in $dH_2O$ to give a concentration of $10^7$ conidia/ml solution. Flasks containing 150 ml of media were inoculated with 200 µl of conidial suspension and incubated with shaking (150 rpm) for 24 h at 37° C. Mycelium was collected by filtering the contents of each flask through Miracloth, snap frozen in liquid $N_2$, and lyophilized.

One mg of LM was suspended in 1 ml of phosphate buffered saline (PBS: 137 mM NaCl, 2.7 mM KCl, 8 mM $Na_2HPO_4$, and 1.5 mM $KH_2PO_4$ [pH7.2]). Six-week-old BALB/c female white mice were given four intraperitoneal injections (300-µl per injection) of immunogen at 2 wk intervals and a single booster injection five days before fusion.

Production and Screening of Hybridomas and Determination of Antibody Specificity.

Hybridoma cell were produced by the method described elsewhere (Thornton, C. R. 2001. Immunological methods for fungi, p. 227-257. In N.J. Talbot (ed.), Molecular and Cellular Biology of Filamentous Fungi, A Practical Approach. University Press, Oxford) and the supernatants were screened by enzyme-linked immunosorbent assay (ELISA) against soluble antigens extracted from LM in PBS and immobilized to the wells of MAXISORP™ (a modified, highly charged polystyrene surface with high affinity to molecules with polar or hydrophilic groups) microtiter plates (50 µl per well). For antibody specificity tests, fungi were grown on SA and surface washings prepared in PBS as described in Thornton (Thornton, C. R. 2001. Immunological methods for fungi, p. 227-257. In N.J. Talbot (ed.), Molecular and Cellular Biology of Filamentous Fungi, A Practical Approach. University Press, Oxford). Protein concentrations, determined spectrophotometrically at 280 nm (NANODROP®, Agilent Technologies Limited, Berkshire, UK), were adjusted to 64 µg/ml buffer, and 50 µl volumes used to coat the wells of microtiter plates. After coating overnight at 4° C., wells were washed four times with PBST (PBS containing 0.05% [vol/vol] TWEEN® 20 (a nonionic detergent)) and once each with PBS and $dH_2O$ and air-dried at 23° C. in a laminar flow hood. The plates were stored in sealed plastic bags at 4° C. in preparation for screening of hybridoma supernatants by ELISA as described below.

ELISA.

Wells containing immobilized antigens were incubated successively with hybridoma supernatant for 1 h, followed with goat anti-mouse polyvalent (immunoglobulin classes IgG, IgA, and IgM) peroxidase conjugate (Sigma Chemical Company, Poole, United Kingdom) diluted 1 in 1000 in PBST for a further hour. Bound antibody was visualised by incubating wells with tetramethyl benzidine substrate solution for 30 min and reactions were stopped by the addition of 3 M $H_2SO_4$. Absorbance values were determined at 450 nm with an MRX automated microplate reader (Dynex Technologies, Billingshurst, UK). Wells were given four 5-min rinses with PBST between incubations. Working volumes were 50 µl per well, and control wells were incubated with tissue culture medium (TCM) containing 10% (vol/vol) fetal calf serum. All incubation steps were performed at 23° C. in sealed plastic bags. The threshold for detection of antigen in ELISA, was determined from control means (2×TCM absorbance values) (Sutula, C. L., J. M. Gillett, S. M. Morrisey, and D. C. Ramsdell. 1986. Interpreting ELISA data and establishing the positive-negative threshold. Plant Dis. 70:722-726). These values were consistently in the range 0.050-0.100. Consequently absorbance values >0.100 were considered as positive for the detection of antigen.

Determination of Ig Subclass and Cloning Procedure.

The Ig class of mAbs was determined with a commercial mouse mAb isotyping kit (ISO-1) according to the manufacturers instructions (Sigma). Hybridoma cells lines were cloned by limiting dilution, and cell lines were grown in bulk in a non-selective medium, preserved by slowly freezing in fetal bovine serum/dimethyl sulfoxide (92:8 [vol/vol]), and stored in liquid nitrogen.

Antigen Purification, Polyacrylamide Gel Electrophoresis and Western Blotting.

Antigen was purified from PBS extracts of LM by affinity chromatography using a Protein A IgG Plus Orientation Kit (Pierce Biotechnology, Rockford, Ill., USA) containing immobilized JF5 mAb. Ascites fluid was prepared from JF5 hybridoma cells in female BALB/c mice (Eurogentec s.a., Belgium). Mice were injected with $10^6$ hybridoma cells washed in PBS and, after 3 wk, approximately 5 ml of ascites fluid was recovered from each mouse and was stored at −20° C. prior to use. For preparation of the affinity column, 15 µl of ascites fluid was mixed with 2 ml of binding buffer and the solution applied to the Protein A-agarose matrix. Crude PBS antigen extract was then incubated with the immobilized antibody and bound antigen was eluted with 0.1 M glycine-HCl (pH2.8) buffer. Polyacrylamide gel electrophoresis (PAGE) was carried out using the system of Laemmli (Laemmli, U. K. 1970. Cleavage of structural proteins during assembly of the head of bacteriophage T4. Nature 227:680-685), with 4-20% (wt/vol) gradient polyacrylamide gels (Bio-Rad Laboratories Limited, Hemel Hempstead, UK), under denaturing conditions. Purified antigen was mixed with Laemmli buffer and denatured by heating at 95° C. for 10 min in the presence of β-mercaptoethanol prior to gel loading. Proteins were separated for 1.5 h at 23° C. (165V). Pre-stained, broad range, markers (Bio-Rad) were used for molecular mass determinations. For westerns, separated proteins were transferred electrophoretically to a PVDF membrane (Bio-Rad). Membranes were washed three times with PBS and then blocked for 16 h at 4° C. with PBS containing 1% (wt/vol) bovine serum albumin (BSA). Blocked membranes were incubated with JF5 mAb supernatant diluted 1 in 2 with PBS containing 0.5% (wt/vol) BSA (PBSA) for 2 h at 23° C. After washing three times with PBS, membranes were incubated for 1 h with goat anti-mouse IgG (whole molecule) alkaline phosphatase conjugate (Sigma) diluted 1 in 15,000 in PBSA. Membranes were washed twice with PBS, once with PBST and bound antibody visualized by incubation in substrate solution. Reactions were stopped by immersion in $dH_2O$ and air-dried between sheets of WHATMAN® filter paper (a cotton liner treated to achieve a minimum alpha cellulose content of 98%). (Modification of the JF5 antigen using peptide-N-glycosidase (PNGase) was carried out prior to electrophoresis and western blotting according to procedures described elsewhere (Bleddyn Hughes, H., R. Carzaniga, S. L. Rawlings, J. R. Green, and R. J. O'Connell. 1999. Spore surface glycoproteins of *Colletotrichum lindemuthianum* are recognized by a monoclonal antibody which inhibits binding to polystyrene. Microbiol. SGM. 145:1927-1936).

Immunofluorescence and Immunogold Electron Microscopy of *A. fumigatus* Conidia and Germlings.

Immunogold labelling was performed with germlings of *A. fumigatus* AF293. Germlings were prepared by incubating washed conidia in normal human serum (BIOSERA®, Ringmer, UK) or in sterile filtered (0.2 µM) 1% (wt/vol) glucose solution for 16 h at 37° C. with gentle mixing. Germlings were pelleted by centrifugation and low temperature embedding of material was carried out as described elsewhere (Thornton, C. R., and N. J. Talbot. 2006. Immunofluorescence microscopy and immunogold EM for investigating fungal infections of plants. Nat. Prot. 5:2506-2511). Immunolabeling was carried with mAb JF5 and goat anti-mouse 20-nm gold conjugate (British Biocell International, Cardiff, Wales) as the secondary reporter molecule. Control grids were incubated with TCM instead of mAb supernatant, but were otherwise treated the same. For IF studies, washed conidia were suspended in glucose solution and transferred to the wells of multiwell slides. After incubation at 37° C. for 16 h, slides were air-dried and fixed as described in Thornton (Thornton, C. R. 2001. Immunological methods for fungi, p. 227-257. In N.J. Talbot (ed.), Molecular and Cellular Biology of Filamentous Fungi, A Practical Approach. University Press, Oxford). Wells were incubated for 1 h with 50 µl of mAb JF5 supernatant or TCM only. Slides were washed three times with PBS with gentle agitation and incubated for a further 30 min with goat anti-mouse polyvalent FITC conjugate (Sigma) diluted 1 in 40 in PBS. Slides were given three 5-min rinses with PBS and the wells overlaid with coverslips mounted in PBS-glycerol mounting medium (Sigma). Slides were examined with a Zeiss Axiophot microscope fitted with epifluorescence, using a UV excitation filter of 365 nm and an absorption filter of 420 nm. All incubation steps were performed at 23° C. in a moist environment and slides were stored at 4° C. in the dark in Petri dishes containing moistened WHATMAN® filter paper no. 1.

Configuration of the LFD. The LFD consisted of G&L Diecut 1734 backing card, WHATMAN® 17chr and 1281 top and sample pads respectively, and WHATMAN® IMMUNOPORE 5 µM nitrocellulose membrane. Monoclonal antibody JF5 was conjugated to 40 nm gold particles, applied to the release pad at 100 units of conjugate/cm, and dried for 16 h at 37° C. The test line antibody consisted of JF5 mAb at 0.5 mg protein/ml of PBS containing 1% (wt/vol) BSA while a commercial rabbit anti-mouse Ig acted as the control line.

Sensitivity and specificity of the LFD. Affinity purified antigen (protein concentrations determined as described) was diluted into normal human serum or PBS and 100 µl samples applied to the LFD. Unspiked serum and PBS acted as the negative controls. Results were recorded after 15 min as positive for the presence of *Aspergillus* antigen (two lines) or negative (single control line only). Specificity of the LFD was determined by growing fungi in normal human serum. Replicate 1 ml serum samples contained in 1.5-ml eppendorf tubes, were inoculated with $10^4$ washed conidia from filamentous fungi (*Aspergillus flavus, A. fumigatus, A. niger, A. terreus, Fusarium solani, Pseudallescheria boydii* and *Rhizopus oryzae*), or an equivalent number of washed yeast cells (*Candida albicans* and *Cryptococcus neoformans*). Tubes were incubated at 37° C. with shaking (100 rpm) for 48 h and fungal propagules precipitated by centrifugation. One hundred-µl samples of neat, cell-free, supernatants were applied to LFD devices and results recorded as described. Growth of filamentous fungi and the yeast *Candida albicans* was determined by visual appraisal of hyphal development or by increases in turbidity of serum samples (*C. neoformans*). Unspiked serum incubated under the same conditions acted as the negative control.

Further tests of LFD specificity were conducted using serum containing the β-lactam antibiotics penicillin-G (Melford Laboratories Limited, Ipswich, UK), amoxicillin (Fluka) and piperacillin (Sigma), the β-lactamase inhibitor tazobactam (Sigma), the cancer prodrug cyclophosphamide (Sigma), and lipoteichoic acids from the bacteria *Enterococcus faecalis* and *Staphylococcus aureus* (both from Sigma). Following reconstitution, 100 µl volumes of solutions containing 5 mg of solid/ml serum (lipoteichoic acids) or 50 mg solid/ml serum (antibiotics, tazobactam and cyclophosphamide) were applied to LFD devices and results recorded as described. Unspiked serum acted as the negative control, while serum samples containing purified antigen and test chemicals acted as positive controls. Three replicates were performed for each test.

LFD detection of antigen in IA sera. The ability of the LFD to detect circulating antigen in humans with IA was tested with sera collected from known or suspected IA patients and from healthy controls. The samples were kindly provided during a blind assessment of assay sensitivity and specificity conducted in collaboration with Dr Elizabeth Johnson (Bristol Health Protection Agency). The samples had previously been tested using the PLATELIA™ GM (galactomannan) EIA (enzyme immunoassay) and a pan-fungal β-glucan test (FUNGITELL®). One hundred-µl samples of undiluted scrum or serum diluted 1 in 10 in normal human serum were applied to LFD devices and the results recorded as described. Three replicates were performed for each sample.

Production of Hybridoma Cell Lines and Isotyping of mAbs.

A single fusion was performed. Cell lines were selected for further study based on the strength of mAb reaction in ELISA. The cell line JF5 was selected and was sub-cloned three times. The monoclonal antibody from the sub-cloned cell line IF5 belonged to the immunoglobulin class G3 (IgG3).

Monoclonal Antibody Specificity Tests.

Monoclonal antibody JF5 was tested for specificity against a wide range of related and unrelated fungi (Table 1). It reacted with antigens from *Aspergillus* species and related fungi from the teleomorphic genera *Emericella, Eurotium* and *Neosartorya*. It cross-reacted with antigens from certain *Penicillium* species, but not with Penicillum species in the subgenus Biverticillium or teleomorphic *Talaromyces* species whose *Penicillium* anamorphs belong to this subgenus. It cross-reacted weakly with antigens from the closely related fungus *Paecilomyces variotti*, but did not react with antigens from a wide range of unrelated fungi including the well-documented invasive pathogens *Candida albicans, Cryptococcus neoformans*, and the emerging pathogens *Fusarium solani, Pseudallescheria boydii* and *Rhizopus oryzae* (Groll, A. H, and T. J. Walsh. 2001. Uncommon opportunistic fungi: new nosocomial threats. Clin. Microbiol. Infect. 7:8-24, Ribes, J. E., C. L. Vanover-Sams, DJ. Baker. 2000. Zygomycetes in human disease. Clin. Microbiol. Rev. 13:236-301, Walsh, T. J., and A. H. Groll. 1999. Emerging fungal pathogens: evolving challenges to immunocompromised patients for the twenty-first century. Transpl. Infect. Dis. 1: 247-261, Walsh, T. J., A. Groll, and J. Hiemenz. 2004. Infections due to emerging and uncommon medically important fungal pathogens. Clin. Microbiol. Infect. 10: 48-66).

Characterisation of the Antigen.

Figure 26:
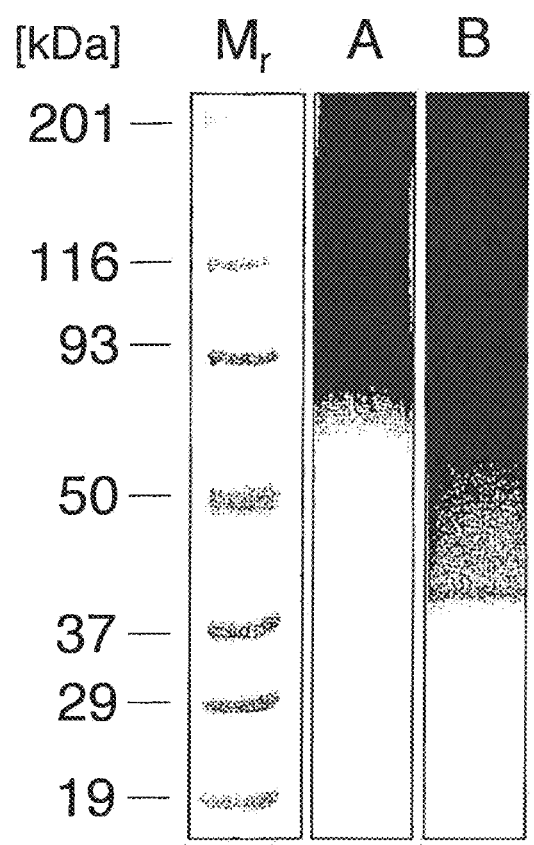
FIG. 26. Analysis of affinity purified antigen by PAGE and Western blotting. M, represents the molecular weight marker.

Polyacrylamide gel electrophoresis and Western blotting. The affinity purified antigen eluted from the column as a single peak containing 0.340 mg protein/ml of buffer. The diffuse binding pattern in Western blotting studies (FIG. 26A) showed that antigen bound by JF5 is glycosylated and is a pattern consistent with binding of mAbs to extracellular glycoproteins in *A. fumigatus* (Stynen, D., J. Sarfati, A. Goris, M.-E. Prevost, M. Lesourd, H. Kamphuis, V. Darras, and J.-P. Latgé. 1992. Rat monoclonal antibodies against *Aspergillus* galactomannan. Inf. Immun. 60:2237-2245). De-glycosylation of the antigen with the enzyme PNGase showed that the protein moiety of the glycoprotein bound by mAb JF5 has an approximate molecular weight of 40 kDa and has an N-glycosylated component (FIG. 26B).

Immunofluorescence and immunogold electron microscopy of conidia and germlings. Immunofluorescence studies showed that the antigen was absent from the surface of ungerminated spores, but was present on the hyphal surface of germlings and was secreted from the hyphal tip (FIG. 27). Immunogold electron microscopy showed that the antigen was present in the hyphal cell wall and in septa and in a capsule-like layer surrounding cells (FIG. 28).

Sensitivity and specificity of the LFD. There was strong detection of the affinity purified antigen in LFD tests (FIG. 29) with an assay sensitivity of 37 ng protein per ml of serum. In PBS only, the sensitivity of the assay was 1.25 ng protein per ml. After 48 h growth of fungi in human serum, there was strong detection of the antigen in serum spiked with 104 conidia of *A. fumigatus* AF293 (FIG. 29) and with other *Aspergillus* species (results not shown). No antigen was detected in serum inoculated with the other fungi tested (FIG. 29), despite prolific growth. No false-positive reactions were exhibited with the S-lactam antibiotics tested or with tazobactam, cyclophosphamide, and bacterial lipoteichoic acids. The chemicals did not inhibit detection of purified antigen (results not shown).

Detection of antigen in IA sera. The JF5 antigen was detected in sera from patients with known or probable IA infection (Table 2). No false negatives were found with sera from healthy individuals. LFD test results were similar to those for GM detection using the PLATELIA™ EIA. However, three of the samples (1655, 1665 and 1667) from patients diagnosed with IA on the basis of clinical symptoms gave positive reactions with the LFD but were negative in the GM test. One of these samples (1655) and two others (samples 1537 and 1538) gave negative LFD reactions when used undiluted but gave positive reactions when diluted ten-fold in normal serum. This was likely due to a high-dose hook effect where high serum antigen concentrations impaired antigen-antibody binding. Results for all other samples were the same when used neat or diluted. Examples of negative and positive reactions with sera are shown in FIG. 29.

TABLE I

Details of organisms and results of ELISA specificity tests

| Organism | Isolate no. | Source[a] | Absorbance (450 nm)[b] |
|---|---|---|---|
| *Absidia corymbifera* | 101040 | CBS | 0.027 |
| *A. glauca* | 1 | CRT | 0.032 |
| *A. spinosa* | 3 | CRT | 0.000 |
| *Acremonium atrogriseum* | 306.85 | CBS | 0.083 |
| *A. blochii* | 424.93 | CBS | 0.006 |
| *Alternaria alternata* | 42 | CRT | 0.000 |
| *Apophysomyces elegans* | 658.93 | CBS | 0.007 |
| Subgenus *Aspergillus* Section *Aspergillus* | | | |
| *Eurotium amstelodami* | 34 | CRT | 0.866 |
| Section *Restricti* | | | |
| *Aspergillus restrictus* | 116.50 | CBS | 0.938 |
| Subgenus *Fumigati* | | | |

TABLE I-continued

Details of organisms and results of ELISA specificity tests

| Organism | Isolate no. | Source[a] | Absorbance (450 nm)[b] |
|---|---|---|---|
| Section *Fumigati* | | | |
| *Aspergillus fumigatus* | 181 | CRT | 1.020 |
| | AFC | CRT | 0.935 |
| | AF293 | SK | 1.213 |
| *Neosartorya fischeri* var. *fischeri* | 681.77 | CBS | 1.105 |
| Section *Cervini* | | | |
| *A. cervinus* | 537.65 | CBS | 0.667 |
| Subgenus *Ornati* | | | |
| Section *Ornati* | | | |
| *A. ornatus* | 184 | CRT | 1.381 |
| (*Hemicarpenteles ornatus*) | | | |
| Subgenus *Clavati* | | | |
| Section *Clavati* | | | |
| *A. clavatus* | 514.65 | CBS | 1.307 |
| Subgenus *Nidulantes* | | | |
| Section *Nidulantes* | | | |
| *A. nidulans* | 542.83 | CBS | 1.133 |
| (*Emericella nidulans* var. *nidulans*) | A4 | FGSC | 1.237 |
| | A26 | FGSC | 1.075 |
| *Emericella quadrilineata* | 591.65 | CBS | 1.045 |
| Section *Versicolores* | | | |
| *Aspergillus versicolor* | 599.65 | CBS | 1.120 |
| Section *Usti* | | | |
| *A. ustus* | 209.92 | CBS | 0.510 |
| Section *Terrei* | | | |
| *A. terreus* var. *terreus* | 601.65 | CBS | 1.186 |
| Section *Flavipedes* | | | |
| *A. niveus* (*Fennelia nivea*) | 261.73 | CBS | 1.085 |
| Subgenus *Circumdati* | | | |
| Section *Wentii* | | | |
| *A. wentii* | 229.67 | CBS | 0.000 |
| Section *Flavi* | | | |
| *A. flavus* | 91856iii | IMI | 1.053 |
| *A. oryzae* | 29 | CRT | 0.963 |
| Section *Nigri* | | | |
| *A. niger* | 102.40 | CBS | 1.433 |
| | 121.49 | CBS | 1.155 |
| | 522.85 | CBS | 1.057 |
| | 553.65 | CBS | 1.066 |
| Section *Circumdati* | | | |
| *A. ochraceous* | 625.78 | CBS | 1.249 |
| Section *Candidi* | | | |
| *A. candidus* | 266.81 | CBS | 0.541 |
| *Aureobasidium pullulans* | 657.76 | CBS | 0.015 |
| *Botrytis cinerea* | R2 | CRT | 0.077 |
| *Candida albicans* | SC5314 | SB | 0.000 |
| *C. dubliniensis* | 8500 | CBS | 0.015 |
| *C. glabrata* | 4692 | CBS | 0.000 |
| *Chaetomium globosum* | 147.51 | CBS | 0.013 |
| *Cladosporium herbarum* | 159.59 | CBS | 0.067 |
| *Cryptococcus neoformans* | 5728 | CBS | 0.010 |
| *C. neoformans* | 7779 | CBS | 0.009 |
| *Cunninghamella bertholletiae* | 182.84 | CBS | 0.012 |
| *Exophiala dermatitidis* | 153.94 | CBS | 0.024 |
| *Fusarium oxysporum* f. sp. *melonis* | 422.90 | CBS | 0.000 |
| *F. oxysporum* f. sp. *pisi* | 260.50 | CBS | 0.005 |
| *F. solani* | 224.34 | CBS | 0.034 |
| *F. solani* | 80 | CRT | 0.056 |
| *F. solani* var. *petrophilum* | 102256 | CBS | 0.006 |
| *F. verticillioides* | 539.79 | CBS | 0.000 |
| *Geotrichum capitatum* | 327.86 | CBS | 0.014 |
| *Mucor fragilis* | 4 | CRT | 0.033 |
| *M. hiemalis* var. *silvaticus* | 50 | CRT | 0.002 |
| *Paecilomyces variotii* | 339.51 | CBS | 0.163 |
| *P. variotii* | 17.1 | CRT | 0.143 |
| *Penicillium brevicompactum* | 210.28 | CBS | 0.571 |
| *P. cinnabarinum* | 39 | CRT | 0.885 |
| *P. chrysogenum* | 105 | CRT | 1.248 |
| *P. citrinum* | 139.45 | CBS | 0.556 |
| *P. cyclopium* | 123.14 | CBS | 0.630 |
| *P. dierckxii* | 250.66 | CBS | 0.629 |
| *P. expansum* | 106 | CRT | 1.141 |
| *P. jensenii* | 43 | CRT | 1.115 |
| *P. islandicum* | 338.48 | CBS | 0.004 |
| *P. marneffei* | 101038 | CBS | 0.093 |
| | 669.95 | CBS | 0.057 |
| *P. melinii* | 218.30 | CBS | 0.486 |
| *P. pupurogenum* | 364.48 | CBS | 0.006 |
| *P. roqueforti* | 221.30 | CBS | 0.347 |
| *P. simplicissimum* | 220.30 | CBS | 0.500 |
| *P. spinulosum* | 108 | CRT | 1.290 |
| *P. variabile* | 385.48 | CBS | 0.037 |
| *Phialophora verrucosa* | 225.97 | CBS | 0.021 |
| *Pseudallescheria boydii* | 835.96 | CBS | 0.004 |
| *Rhizomucor miehei* | 360.92 | CBS | 0.005 |
| *Rhizopus microsporus* var. *rhizopodiformis* | 102277 | CBS | 0.020 |
| *R. oryzae* | 146.90 | CBS | 0.016 |
| *R. oryzae* | 395.54 | CBS | 0.010 |
| *R. sexualis* var. *sexualis* | 209090 | IMI | 0.000 |
| *R. stolonifer* | G1 | CRT | 0.000 |
| *Saksenaea vasiformis* | 133.90 | CBS | 0.030 |
| *Scedosporium prolificans* | 742.96 | CBS | 0.010 |
| *S. prolificans* | 100391 | CBS | 0.025 |
| *Stachybotrys chartarum* | 485.48 | CBS | 0.017 |
| *Talaromyces flavus* | 437.62 | CBS | 0.051 |
| *T. stipitatus* | 266.91 | CBS | 0.046 |
| *Trichoderma longibrachiatum* | 446.95 | CBS | 0.000 |
| *T. pseudokoningii* | 500.94 | CBS | 0.000 |
| *Verticillium coccosporum* | GD2/B8 | CRT | 0.000 |
| *Wallemia sebi* | 196.56 | CBS | 0.043 |

[a]CBS = Centraalbureau voor Schimmelcultures, PO Box 85167, 3508 AD Utrecht, The Netherlands; FGSC = Fungal Genetics Stock Centre, University of Missouri, 5007 Rockhill Road, Kansas City, MO 64110, USA; CRT = C. R. Thornton; IMI = International Mycological Institute, Egham, England; SB = S. Bates, School of Biosciences, University of Exeter; SV = S. Krappman, Institute of Microbiology and Genetics, Department of Molecular Microbiology and Genetics, Georg-August-University, Gottingen, Germany.

[b]Each value represents the mean of replicated values. Threshold absorbance value for detection of antigen: ≥0.100.

TABLE 2

Results of LFD tests of serum samples from healthy individuals or from patients with known or suspected invasive aspergillosis

| Specimen number | Invasive Aspergillosis[a] | Platelia GM index value | Platelia GM result | Fungitell β-glucan concentration (pg/mL) | Fungitell result | LF res |
|---|---|---|---|---|---|---|
| 6OHD | No | — | — | 45.90 | Negative | − |
| 7OHD | No | — | — | 42.40 | Negative | − |
| 8OHD | No | — | — | 44.30 | Negative | − |
| 9OHD | No | — | — | 44.09 | Negative | − |
| 813 | Yes | 0.12 | Negative | 128.35 | Positive | − |
| 815 | Yes | 0.36 | Negative | 360.49 | Positive | − |
| 1263 | Yes | 0.16 | Negative | 111.72 | Positive | − |
| 1652 | Yes | 0.32 | Negative | 111.94 | Positive | − |
| 1655 | Yes | 0.35 | Negative | 104.13 | Positive | +[c] |
| 1657 | Yes | 0.71 | Positive | 122.23 | Positive | +/− |
| 1665 | Yes | 0.16 | Negative | 108.28 | Positive | +/− |
| 1667 | Yes | 0.30 | Negative | 142.19 | Positive | +/− |
| 1130 | Probable | 2.04 | Positive | 85.51 | Equivocal | + |
| 1131 | Probable | 1.52 | Positive | 219.61 | Positive | + |
| 1537 | Probable | 4.64 | Positive | 782.95 | Positive | +[b] |
| 1538 | Probable | 4.64 | Positive | >500 | Positive | +[c] |

[a] Proven or probable cases of disease formally classified according to EORTC criteria
[b] Reactions in LFD tests: − (no antigen detected), +/− (weak reaction), + (strong reaction). Results from specimens 9OHD, 1657 and 1131 are shown in FIG. 29.
[c] Samples with a strong reaction at a 1 in 10 dilution in normal serum, but negative undiluted Example 2

Summary

Lectin binding studies show that the antigen(s) bound by MAb JF5 is/are immunogenic N-linked mannoprotein(s) comprising terminal non-reducing mannose residues linked α1-3 and α1-6. Insensitivity of the antigen(s) in ELISA to mild alkaline hydrolysis (β-elimination) shows that the MAb does not bind to glycan structures O-linked through serine and threonine.

Methodology

Lectin binding studies. Antigen(s) were purified from *Aspergillus fumigatus* using the method described. Purified antigen solution was subjected to glycoprotein fractionation using a QPROTEOME™ Mannose Glycoprotein Kit (Catalog no. 37551; Qiagen Ltd., Crawley, UK) according to the manufacturer's instructions. The ConA, GNA, and LCH lectin spin columns in the kit allow specific enrichment of glycoproteins with mannose-rich glycan moieties. The three lectins each bind different subclasses of these moieties. ConA binds biantennary and triantennary complex type N-glycans; LCH binds biantennary and triantennary complex type N-glycans with core fucose. GNA binds α1-3 and α1-6 linked high mannose structures.

Flow-through and eluted fractions from the lectin spin columns were assayed by Western blotting. Polyacrylamide gel electrophoresis (PAGE) was carried under denaturing conditions, with 4-20% (wt/vol) gradient polyacrylamide gels (Bio-Rad Laboratories Limited, Hemel Hempstead, UK). Fractions were mixed with Laemmli buffer and denatured by heating at 95° C. for 10 min in the presence of 3-mercaptoethanol prior to gel loading. Each well was loaded with 0.5 mg of protein. Glycoproteins were separated for 1.5 h at 23° C. (165V) and pre-stained, broad range, markers (Bio-Rad) were used for molecular mass determinations. For Westerns, separated proteins were transferred electrophoretically to a PVDF membrane (Bio-Rad). The membranes were blocked for 16 h at 4° C. with PBS containing 1% (wt/vol) bovine serum albumin (BSA) and incubated with JF5 MAb supernatant diluted 1 in 2 with PBS containing 0.5% (wt/vol) BSA (PBSA) for 2 h at 23° C. After washing three times with PBS, the membrane was incubated for 1 h with goat anti-mouse IgG (whole molecule) alkaline phosphatase conjugate (Sigma) diluted 1 in 15,000 in PBSA. The membrane was washed twice with PBS, once with PBST and bound antibody visualized by incubation in substrate solution. Reactions were stopped by immersion in dH$_2$O and air-dried between sheets of WHATMAN® filter paper.

Mild alkaline hydrolysis (β-elimination). Mild alkaline hydrolysis results in cleavage of glycans O-linked through the β-hydroxy amino acids serine and threonine. It does not cleave glycans N-linked through asparagine. Chemical modification of the purified antigen was carried out according the procedure described in Thornton (Thornton, C. R. 2001. Immunological methods for fungi, p. 227-257. In NJ. Talbot (ed.), Molecular and Cellular Biology of Filamentous Fungi, A Practical Approach. University Press, Oxford). Briefly, purified antigen was immobilized to the wells of MAXISORP™ microtitre plates. The wells were incubated with 50 µl of a 50 mM solution of NaOH or were incubated with 50 µl of dH$_2$O only (control). After incubation for 24 h at 23° C., the wells were washed three times (3 min each time) with PBS and assayed by Enzyme-Linked Immunosorbent Assay (ELISA) with MAb JF5 as described.

Results and Discussion

Lectin binding studies. Western blotting analysis of flow-through and eluate fractions from lectin spin columns show that the JF5 antigen(s) has/have a high affinity for the mannose-binding lectin (GNA) from *Galanthus nivalis* (snowdrop) (FIG. 30). No binding or very weak binding only was found with the other two mannose-binding lectins, ConA from *Canavalia ensiformis* (jack bean) or LCH from *Lens culinaris* (lentil), respectively. GNA lectin is unique in that it is specific for D-mannose groups only (unlike ConA that is a mannose/glucose-specific lectin), especially those possessing Man(α1-3)Man units. It displays selective reactivity with mannans or mannose-containing glycoproteins and has a strict requirement for non-reducing terminal mannose units (Shibuya, N., I. J. Goldstein, E. J. M. Van Damme, and W. J. Peumans, 1988. Binding Properties of a Mannose-specific Lectin from the Snowdrop (*Galanthus nivalis*) Bulb. J. Biol. Chem. 263:728-734). Poor binding of the JF5 antigen to LCH and ConA lectins shows that the antigen(s) is/are not hybrid type or bi- and tri-antennary complex type N-linked glycoproteins.

Mild alkaline hydrolysis (0-elimination). ELISA studies using chemical modification of the purified antigen with mild alkali show that the MAb does not bind to glycan structures O-linked through serine and threonine. There was no significant difference (Student's t-test; t=0.113, not significant) between the absorbance values obtained with treated antigen(s) (1.378*0.009) compared to the control (1.376±0.013).

N-terminal sequencing. The N-terminal sequence (AL-FALAKXV) of the protein component of the purified antigen was shown to have significant homology to the protein Cwp1p from the yeast *Saccharomyces cerevisiae* (GenBank accession number EEU05173.1). Cwp1p is a cell wall mannoprotein, linked to a β-1,3- and β-1,6-glucan heteropolymer through a phosphodiester bond (Van Der Vaart, J. M., L. H. P. Caro, J. W. Chapman, F. M. Klis, and C. T. Verrips, 1995. Identification of three mannoproteins in the cell wall of *Saccharomyces cerevisiae*. J. Bacteriol. 177:3104-3110). Using protein subcellular localization prediction software, the Cwp1p glycoprotein is predicted to have a signal peptide, to be secreted and to be extracellular. Despite homology of the protein component to yeast Cwp1p, monoclonal antibody JF5 retains its specificity for *Aspergillus* species. It does not cross-react with *S. cerevisiae*.

Example 3

Detection of Invasive Pulmonary Aspergillosis by Lateral Flow Technology Compared to Galactomannan and (1→3)-β-D-Glucan Early diagnosis of invasive aspergillosis is critical for the initiation of appropriate antifungal therapy and may improve outcomes in high-risk patients. The use of sensitive biomarkers, including the non-invasive assays for galactomannan and (1→3)-β-D-glucan, also reduces the use of unnecessary antifungal agents. Despite their advantages, the galactomannan and the (1→3)-β-D-glucan assays are confined to laboratories equipped for these tests or require samples be sent to reference laboratories. Lateral-flow technology incorporates immunochromatographic assays into simple devices for point-of-care diagnosis. When coupled to a monoclonal antibody specific to an extracellular glycoprotein of *Aspergillus* this technology is a sensitive and specific biomarker (Thornton, C. R. 2008. Development of an Immunochromatographic Lateral-Flow Device for Rapid Serodiagnosis of Invasive Aspergillosis. Clin. Vacc. Immunol. 15:1095-1105). Our objective was to evaluate the time to positivity and sensitivity of a lateral-flow device in an established guinea pig model of invasive pulmonary aspergillosis, and directly compare these results to those obtained using the galactomannan and (1→3)-β-D-glucan assays.

Immunosuppressed male Hartley guinea pigs (Charles River Laboratories) were exposed to conidia for 1 hour in an aerosol chamber. Serum samples were collected on days 3, 5, and 7 post-inoculation. A previously described lateral-flow device was used for the serodiagnosis of invasive aspergillosis (Thornton, C. R. 2008. Development of an Immunochromatographic Lateral-Flow Device for Rapid Serodiagnosis of Invasive Aspergillosis. Clin. Vacc. Immunol. 15:1095-1105). Briefly, an IgG monoclonal antibody (JF5) to an epitope on an extracellular antigen secreted constitutively during active growth of *Aspergillus* was immobilized to a capture zone on a porous nitrocellulose membrane. JF5 IgG was also conjugated to colloidal gold particles to serve as the detection reagent. Serum was added to a release pad containing the antibody-gold conjugate, which bound the target antigen, then passed along the porous membrane and bound to JF5 IgG monoclonal antibody immobilized in the capture zone. Test results were available within 10-15 minutes after loading the sample. Bound antigen-antibody-gold complex were observed as a red line with an intensity proportional to the antigen concentration, and were classified as negative, weakly positive, moderately positive, or strongly positive (FIGS. 31A, B, C, and D). Anti-mouse immunoglobulin immobilized to the membrane in a separate zone served as an internal control.

The (1→3)-β-D-glucan assay was performed using a commercially available kit (FUNGITELL®, Associates of Cape Cod). Serum was transferred in duplicate to a 96-well cell culture tray and processed according to the manufacturer's instructions. The mean rate of change in optical density (OD) at 405 nm over time was measured using a microplate spectrophotometer (SYNERGY™ HT; Biotek Instruments) and unknowns were interpolated from a standard curve. Serum galactomannan was measured using a commercially available kit (PLATELIA™ *Aspergillus* EIA, Bio-Rad Laboratories). Serum was heat-treated following the addition of an EDTA acid solution. Treated supernatant was added to microwells containing conjugate and the rat monoclonal antibody EB-A2. Following incubation, microwells were washed and the substrate solution added forming a complex with the monoclonal antibody. The OD values of each sample, positive control, negative control, and cut-off control were measured using a microplate spectrophotometer at 450 and 630 nm, and the galactomannan index (OMI) was calculated as the OD of each sample divided by the mean cut-off of the control. The lateral-flow assay and the (1→3)-β-D-glucan and galactomannan assays were performed in separate laboratories by different investigators blinded to the results of the other.

For each biomarker, the time to positivity was defined as the first time point at which three serum samples became positive. Time to positivity was plotted by Kaplan-Meier analysis, and differences in median time at which the assays became positive were analyzed by the log-rank test. Differences in the number of positive samples per time point between the assays were determined by Fisher's exact test. The overall specificity of each assay was also measured in uninfected controls. All statistical tests were performed using Prism 5.0 (GraphPad Software, Inc.).

The assays were negative 1 hour post-inoculation prior to the onset of invasive disease with the exception of a galactomannan test result (Table 3), which likely represents a false positive result, as invasive disease is not yet established. Each biomarker became positive early with more than three samples positive for each assay by day 5 post-inoculation. In serial samples from the same animals, each biomarker continued to increase throughout the study (FIGS. 32A, B, and C). When the weakly positive lateral-flow device results were considered positive, this assay became positive on day 3, which was significantly shorter compared to the galactomannan (day 5, p=0.03) and (1→3)-β-D-glucan assays (day 7, p<0.001). When the weakly positive lateral-flow results were considered negative and only the moderately and strongly positive results positive, the time to positivity for each biomarker assay occurred at the day 5 time point.

The sensitivity of each biomarker increased throughout the study period (Table 3). Similar to the time to positivity results, when the weakly positive results were considered positive, the sensitivity of the lateral-flow device on day 3 (48%) was greater than the galactomannan (4%, p<0.001) and (1→3)-β-D-glucan glucan assays (0%, p<0.001). The sensitivity of the lateral-flow device also remained higher than the (1→3)-β-D-glucan assay on day 5 (82% vs. 23%, respectively; p<0.001), but was not significantly different than the galactomannan assay (59%). When the weakly positive lateral-flow device results were considered negative and only the moderately to strongly positive results positive, the sensitivity of this biomarker was similar to that of the galactomannan and (1→3)-β-D-glucan assays (35%, 59%, and 23%, respectively; p>0.05). Each biomarker was 100% sensitive at the day 7 time point. Excellent specificity was also observed for each biomarker with only two false positives observed in uninfected animals with the (1→3)-β-D-glucan assay (Table 3).

TABLE 3

Comparison of the lateral flow device and galactomannan and (1→3)-β-D-glucan assays

| Time Point | Lateral-Flow Device (+) | Beta-glucan (≥80 pg/mL) | Galactomannan Index (≥0.5) |
|---|---|---|---|
| 1 hour | | | |
| Number positive | 0/5 | 0/5 | 1/5 |
| Day 3 | | | |
| Number positive | 12/25 | 0/25 | 1/25 |
| Sensitivity | 48% | 0% | 4% |
| Day 5 | | | |
| Number positive | 14/17 | 4/17 | 10/17 |
| Sensitivity | 82% | 23% | 59% |
| Day 7 | | | |
| Number positive | 6/6 | 6/6 | 6/6 |
| Sensitivity | 100% | 100% | 100% |
| Uninfected | 0/10 | 2/10 | 0/16 |
| Specificity | 100% | 80% | 100% |

The table below discloses the "DNA Sequences" as SEQ ID NOS 1, 3, 5, 38, 7, 9, 12, 14, and 16 and the "Amino Acid Sequences" as SEQ ID NOS 26-34, 36, and 37, all respectively, in order of appearance.

| Reference | DNA Sequence | Amino Acid Sequence |
|---|---|---|
| VH3-1 | AGCTTCTCGAGTCTGGAGGTGCCCTGTGCAGCCTGAGGATCCCTGAGGATCCCTGTG CAGCCCTCAGGATTCGATTTTAGTAGATACTGGATGAGTTGGGTCCGGCAGGCTCCAGGGA AAGGGCTAGAATGGATTGGAGAAATTAATCCAGATAGCAGTAAGATAAATATGCCA TCTCTAAAGGATAAATTCATCATCTCCAGAGACAACGCCAAAAATACGCTGTACCTGCAA ATGAGCAAAGTGAGATCTGAGGACACAGCCCTTTATTACTGTGCAAGACCTCGGGGTTAC TACGCTATGGACTTCTGGGGTCAAGGAACCTCAGTCACCGTCTCCTCAGCTACAACAACA GCCCCATCCGTCTTCCCCCTGGCAC | MDFGLIFFIVALLKGVQCEVKLLESGGGLVQ PGGSLKLSCAASGFDFSRYWMSWVRQAPGK GLEWIGEINPDSSKINYMPSLKDKFIISRDNA KNTLYLQMSKVRSEDTALYYCARPRGYYA MDFWGQGTSVTVSSATTTAPSVFPLA |
| VH3-2 | AGCTTCTCGAGTCTGGAGGTGCCCTGTGCAGCCTGAGGATCCCTGTGCAGCCTGAGGATCCCTGTG CAGCCCTCAGGATTCGATTTTAGTAGATACTGGATGAGTTGGGTCCGGCAGGCTCCAGGGA AAGGGCTAGAATGGATTGGAGAAATTAATCCAGATAGCAGTAAGATAAATATGCCA TCTCTAAAGGATAAATTCATCATCTCCAGAGACAACGCCAAAAATACGCTGTACCTGCAA ATGAGCAAAGTGAGATCTGAGGACACAGCCCTTTATTACTGTCAAGACCTCGGGGTTAC TACGCTATGGACTTCTGGGGTCAAGGAACCTCAGTCACCGTCTCCTCAGCTACAACAACA GCCCCATCCGTCTTCCCCCTGGCAC | MDFGLIFFIVALLKGVQCEVKLLESGGGLVQ PGGSLKLSCAASGFDFSRYWMSWVRQAPGK GLEWIGEINPDSSKINYMPSLKDKFIISRDNA KNTLYLQMSKVRSEDTALYYCARPRGYYA MDFWGQGTSVTVSSATTTAPSVFPLA |
| VH3-4 | ATGGATTTTGGGCTGATTTTTTTTATTGTCGTCAGCCTGGAGGTCCAGTGTGAGGTGA AGCTTCTCGAGTCTGGAGGTGCCCTGTGCAGCCTGAGGATCCCTGAGGATCCCTGTG CAGCCCTCAGGATTCGATTTTAGTAGATACTGGATGAGTTGGGTCCGGCAGGCTCCAGGGA AAGGGCTAGAATGGATTGGAGAAATTAATCCAGATAGCAGTAAGATAAATATGCCA TCTCTAAAGGATAAATTCATCATCTCCAGAGACAACGCCAAAAATACGCTGTACCTGCAA ATGAGCAAAGTGAGATCTGAGGACACAGCCCTTTATTACTGTCAAGACCTCGGGGTTAC TACGCTATGGACTTCTGGGGTCAAGGAACCTCAGTCACCGTCTCCTCAGCTACAACAACA GCCCCATCCGTCTTCCCCCTGGCAC | MDFGLIFFIVALLKGVQCEVKLLESGGGLVQ PGGSLKLSCAASGFDFSRYWMSWVRQAPGK GLEWIGEINPDSSKINYMPSLKDKFIISRDNA KNTLYLQMSKVRSEDTALYYCARPRGYYA MDFWGQGTSVTVSSATTTAPSVFPLA |
| VH3-8 | ATGGATTTTGGGCTGATTTTTTTTATTGTCGTCAGCCTGGAGGTCCAGTGTGAGGTGA AGCTTCTCGAGTCTGGAGGTGCCCTGTGCAGCCTGAGGATCCCTGAGGATCCCTGTG CAGCCCTCAGGATTCGATTTTAGTAGATACTGGATGAGTTGGGTCCGGCAGGCTCCAGGGA AAGGGCTAGAATGGATTGGAGAAATTAATCCAGATAGCAGTAAGATAAATATGCCA TCTCTAAAGGATAAATTCATCATCTCCAGAGACAACGCCAAAAATACGCTGTACCTGCAA ATGAGCAAAGTGAGATCTGAGGACACAGCCCTCTATTACTGTCAAGACCTCGAGGTTAC TACGCTATGGACTTCTGGGGTCAAGGAACCTCAGTCACCGTCTCCTCAGCTACAACAACA GCCCCATCCGGTCTCCCCCTGGCGC | MDFGLIFFIVALLKGVQCEVKLLESGGGLVQ PGGSLKLSCAASGFDFSRYWMSWVRQAPGK GLEWIGEINPDSSKINYMPSLKDKFIISRDNA KNTLYLQMSKVRSEDTALYYCARPRGYYA MDFWGQGTSVTVSSATTTAPSVPWR |
| VH5-1 | ATGGATTTTGGGCTGATTTTTTTTATTGTCGTCAGCCTGGAGGTCCAGTGTGAGGTGA AGCTTCTCGAGTCTGGAGGTGCCCTGTGCAGCCTGAGGATCCCTGAGGATCCCTGTG CAGCCCTCAGGATTCGATTTTAGTAGATACTGGATGAGTTGGGTCCGGCAGGCTCCAGGGA AAGGGCTAGAATGGATTGGAGAAATTAATCCAGATGGCAGTAAGATAAATATGCCA TCTCTAAAGGATAAATTCATCATCTCCAGAGACAACCCCAAAAATACTGTACCTGCAA ATGAGCAAAGTGAGATCTGAGGACACAGCCCTTATTACTGCAGTCCGTCTCCTCAGCTACAACAACA GCCCCACCCGTCATCCACTGGTCCCTGAAGCTTGG | MDFGLIFFIVALLKGVQCEVKLLESGGGLVQ PGGSLKLSCAASGFDFSRYWMSWVRQAPGK GLEWIGEINPDGSKINYMPSLKDKFIISRDNA KNTLYLQMSKVRSEDTALYYCARPRGYYA MDFWGQGTSVTVSSATTTAPPVVPLVPEAW |
| VH5-2 | ATGGATTTTGGGCTGATTTTTTTTATTGTCGTCAGCCTGGAGGTCCAGTGTGAGGTGA AGCTTCTCGAGTCTGGAGGTGCCCTGTGCAGCCTAGTAGATACTGGATGAGTTGGGTCCGGCAGGCTCCAGGGA | MDFGLIFFIVALLKGVQCEVKLLESGGGLVQ PGGSLKLSCAASGFDFSRYWMSWVRQAPGK GLEWIGEINPDSSKINYMPSLKDKFIISRDNA |

| Reference | DNA Sequence | Amino Acid Sequence |
|---|---|---|
| | AAGGGCTAGAATGGATTGGAGAAATTAATCCAGATAGCAGTAAGATAAACTATATGCCA TCTCTAAAGGATAAATTCATCATCTCCAGAGACAACGCCAAAAATACGCTGTACCTGCAA ATGAGCAAAGTGAGATCTGAGGACACAGCCCTTTATTACTGTCCAAGACCTCGGGGTTAC TACGCTATGGACTTCTGGGGTCAAGGAACCTCAGTCACCGTCTCCTCAGCTACAACAACA GCCCCACCCGTCTATCCCCTGGCCCCTGG | KNTLYLQMSKVRSEDTALYYCARPRGYYA MDFWGQGTSVTVSSATTAPPVVPLAP |
| JF5VH Consensus Sequence | | MDFGLIFFIVALLKGVQCEVKLLESGGGLVQ PGGSLKLSCAASGFDFSRYWMSWVRQAPGK GLEWIGEINPDSKINYMPSLKDKFIISRDNA KNTLYLQMSKVRSEDTALYYCARPRGYYA MDFWGQGTSVTVSSATTTAPSVFPLA |
| VL4-1 | ATGGAGTCACATACCCAGGTCTTTGTTTCTCTGGTTGTCTGGTTGACGGAG ACATTGTGATGACCCAGTCTCACAAAGTCATGTCCACATCAGTAGGAGACAGGGTCAGCA TCACCTGCAAGGCCAGTCAGGATGTGAGTACTGCTGTAGCCTGGTACCAGCAGAAACCA GGACAATCTCCTAAACCACTGATTTACTGGGCATCCACTAGCCTACCAGTACACTGGAGTCCCTGAT CGCTTCACTGGCAGTGGATCTGGGACGGATTTCACTTTCACCATCAGCAGTGTGCAGGCT GAAGACCTGGCAGTTTATTACTGTCAGCAACATTACAGTATTCCGTGGACGTTCGGTGGA GGCACCAAGCTGGAAATCAAACGGGCTGATGCTGCACCAACTGTATCCATCTTCCCACCA TCCAGTAAGCTTGGG | MESHTQVFIFVFLWLSGVDGDIVMTQSHKV MSTSVGDRVSITCKASQDVSTAVAHQQKP GQSPKPLIYSASYQYTGVPDRFTGSGSTDFT FTISSVQAEDLAVYYCQQHYSIPWTFGGGTK LEIKRADAAPTVSIFPPSSKLG |
| VL4-8 | ATGGAGACACAGTCTCAGGTCTTTGTATTCGTTTTCTCTGGTTGTCTGGTTGACGGAG ACATTGTGATGACCCAGTCTCACAAAGTCATGTCCACATCAGTAGGAGACAGGGTCAGCA TCACCTGCAAGGCCAGTCAGGATGTGAGTACTGCTGTAGCCTGGTACCAGCAGAAACCA GGACAATCTCCTAAACCACTGATTTACTGGGCATCCACTAGCCTACCAGTACACTGGAGTCCCTGAT CGCTTCACTGGCAGTGGATCTGGGACGGATTTCACTTTCACCATCAGCAGTGTGCAGGCT GAAGACCTGGCAGTTTATTACTGTCAGCAACATTACAGTATTCCGTGGACGTTCGGTGGA GGCACCAAGCTGGAAATCAAACGGGCTGATGCTGCACCAACTGTATCCATCTTCCCACCA TCCAGTAAGCTTGGG | METQSQVFVFVFLWLSGVDGDIVMTQSHKV MSTSVGDRVSITCKASQDVSTAVAHQQKP GQSPKPLIYSASYQYTGVPDRFTGSGSTDFT FTISSVQAEDLAVYYCQQHYSIPWTFGGGTK LEIKRADAAPTVSIFPPSSKLG |
| VL4-18 | CCCAGGTCTTTGTATTGGTGTTTCTCTGGTTGTCTGTGTTGACGGAGACATTGTGATGAC CCAGTCTCACAAAGTCATGTCCACATCAGTAGGAGACAGGGTCAGCATCACCTGCAAGG CCAGTCAGGATGTGAGTACTGCTGTAGCCTGGTACCAGCAGAAACCAGGACAATCTCCTA AACCACTGATTTACTGGGCATCCACTAGCCTCTACCAGTACACTGGAGTCCCTGATCGCTTCACTGGCA GTGGATCTGGGACGGATTTCACTTTCACCATCAGCAGTGTGCAGGCTGAAGACCTGGCAG TTTATTACTGTCAGCAACATTACAGTATTCCGTGGACGTTCGGTGGAGGCACCAAGCTGG AAATCAAACGGGCTGATGCTGCACCAACTGTATCCATCTTCCCACCATCCAGTAAGCTTG GG | QVFVLVFLWLSGVDGDIVMTQSHKVMSTSV GDRVSITCKASQDVSTAVAHQQKPGQSPK PLIYSASYQYTGVPDRFTGSGSTDFTFTISSV QAEDLAVYYCQQHYSIPWTFGGGTKLEIKR ADAAPTVSIFPPSSKLG |
| JF5VL Consensus Sequence | | MESXSQVFVFVFLWLSGVDGDIVMTQSHKV MSTSVGDRVSITCKASQDVSTAVAHQQKP GQSPKPLIYSASYQYTGVPDRFTGSGSTDFT FTISSVQAEDLAVYYCQQHYSIPWTFGGGTK LEIKRADAAPTVSIFPPSSKLG |

The invetion claimed is:

1. A hybridoma deposited under accession number ECACC 08120202.

2. An antibody capable of specifically binding to *Aspergillus*, which may be obtained by culture of the hybridoma of claim 1.

3. A method of assaying for the presence of an *Aspergillus* species in a sample, comprising:

a) contacting the sample with labeled antibodies according to claim 2; and b) observing the sample for binding of the antibodies to epitopes in the sample;

wherein binding of the antibodies is indicative of the presence of an *Aspergillus* species.

\* \* \* \* \*

UNITED STATES PATENT AND TRADEMARK OFFICE
CERTIFICATE OF CORRECTION

PATENT NO. : 11,142,568 B2
APPLICATION NO. : 16/518565
DATED : October 12, 2021
INVENTOR(S) : Christopher Thornton It is certified that error appears in the above-identified patent and that said Letters Patent is hereby corrected as shown below:

On the Title Page

Item (73) Assignee: Change "The University of Exeter" to -- University of Exeter --

Signed and Sealed this
Thirteenth Day of June, 2023

Katherine Kelly Vidal
*Director of the United States Patent and Trademark Office*

SEQUENCE LISTING

<160> NUMBER OF SEQ ID NOS: 39

<210> SEQ ID NO 1
<211> LENGTH: 445
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggattttg ggctgatttt ttttattgtt gctcttttaa aagggtcca gtgtgaggtg      60 aagcttctcg agtctggagg tggcctggtg cagcctggag atccctgaa actctcctgt    120 gcagcctcag gattcgattt tagtagatac tggatgagtt gggtccggca ggctccaggg    180
aaagggctag aatggattgg agaaattaat ccagatagca gtaagataaa ctatatgcca    240
tctctaaagg ataaattcat catctccaga gacaacgcca aaaatacgct gtacctgcaa    300
atgagcaaag tgagatctga ggacacagcc ctttattact gtgcaagacc tcggggttac    360
tacgctatgg acttctgggg tcaaggaacc tcagtcaccg tctcctcagc tacaacaaca    420
gccccatccg tcttcccccct ggcac                                         445

<210> SEQ ID NO 2
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<223> OTHER INFORMATION: See specification as filed for detailed
      description of substitutions and preferred embodiments

<400> SEQUENCE: 2

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Xaa
        35                  40                  45

Ser Arg Tyr Trp Met Ser Trp Val Arg Gln Ala Pro Gly Lys Gly Leu
    50                  55                  60

Glu Trp Ile Gly Glu Ile Asn Pro Asp Xaa Ser Ser Lys Ile Asn Tyr
65                  70                  75                  80

Met Pro Ser Leu Lys Asp Lys Phe Ile Ile Ser Arg Asp Asn Ala Lys
                85                  90                  95

Asn Thr Leu Tyr Leu Gln Met Ser Lys Val Arg Ser Glu Asp Thr Ala
            100                 105                 110

Leu Tyr Tyr Cys Ala Arg Pro Arg Gly Tyr Xaa Tyr Ala Met Asp Phe
        115                 120                 125

```
Trp Gly Gln Gly Thr Ser Val Thr Val Ser Ser Ala Thr Thr Thr Ala
            130                 135                 140

Pro Ser Val Phe Pro Leu Ala
145                 150
```

<210> SEQ ID NO 3
<211> LENGTH: 445
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atggattttg ggctgatttt ttttattgtt gctcttttaa aaggggtcca gtgtgaggtg      60
aagcttctcg agtctggagg tggcctggtg cagcctggag atccctgaa actctcctgt     120 gcagcctcag gattcgattt tagtagatac tggatgagtt gggtccggca ggctccaggg    180
aaagggctag aatggattgg agaaattaat ccagatagca gtaagataaa ctatatgcca    240
tctctaaagg ataaattcat catctccaga gacaacgcca aaaatacgct gtacctgcaa    300
atgagcaaag tgagatctga ggacacagcc ctttattact gtgcaagacc tcggggttac    360
tacgctatgg acttctgggg tcaaggaacc tcagtcaccg tctcctcagc tacaacaaca    420
gccccatccg tcttcccct ggcac                                           445
```

<210> SEQ ID NO 4
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<223> OTHER INFORMATION: See specification as filed for detailed
      description of substitutions and preferred embodiments

<400> SEQUENCE: 4

```
Met Asp Phe Gly Leu Ile Phe Phe Ile Val Ala Leu Leu Lys Gly Val
1               5                  10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Xaa
        35                  40                  45

Ser Arg Tyr Trp Met Ser Trp Val Arg Gln Ala Pro Gly Lys Gly Leu
    50                  55                  60

Glu Trp Ile Gly Glu Ile Asn Pro Asp Xaa Ser Ser Lys Ile Asn Tyr
65                  70                  75                  80

Met Pro Ser Leu Lys Asp Lys Phe Ile Ile Ser Arg Asp Asn Ala Lys
                85                  90                  95

Asn Thr Leu Tyr Leu Gln Met Ser Lys Val Arg Ser Glu Asp Thr Ala
            100                 105                 110
```

```
Leu Tyr Tyr Cys Ala Arg Pro Arg Gly Tyr Xaa Tyr Ala Met Asp Phe
            115                 120                 125

Trp Gly Gln Gly Thr Ser Val Thr Val Ser Ser Ala Thr Thr Thr Ala
        130                 135                 140

Pro Ser Val Phe Pro Leu Ala
145                 150

<210> SEQ ID NO 5
<211> LENGTH: 445
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggattttg ggctgatttt ttttattgtt gctctttta aaggggtcca gtgtgaggtg       60
aagcttctcg agtctggagg tggcctggtg cagcctggag gatccctgaa actctcctgt    120
gcagcctcag gattcgattt tagtagatac tggatgagtt gggtccggca ggctccaggg    180
aaagggctag aatggattgg agaaattaat ccagatagca gtaagataaa ctatatgcca    240
tctctaaagg ataaattcat catctccaga gacaacgcca aaaatacgct gtacctgcaa    300
atgagcaaag tgagtctga ggacacagcc ctttattact gtgcaagacc tcggggttac    360
tacgctatgg acttctgggg tcaaggaacc tcagtcaccg tctcctcagc tacaacaaca    420
gccccatccg tcttcccccct ggcac                                          445

<210> SEQ ID NO 6
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<223> OTHER INFORMATION: See specification as filed for detailed
      description of substitutions and preferred embodiments

<400> SEQUENCE: 6

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Xaa
        35                  40                  45

Ser Arg Tyr Trp Met Ser Trp Val Arg Gln Ala Pro Gly Lys Gly Leu
    50                  55                  60

Glu Trp Ile Gly Glu Ile Asn Pro Asp Xaa Ser Ser Lys Ile Asn Tyr
65                  70                  75                  80

Met Pro Ser Leu Lys Asp Lys Phe Ile Ile Ser Arg Asp Asn Ala Lys
```

```
                    85                  90                  95

Asn Thr Leu Tyr Leu Gln Met Ser Lys Val Arg Ser Glu Asp Thr Ala
            100                 105                 110

Leu Tyr Tyr Cys Ala Arg Pro Arg Gly Tyr Xaa Tyr Ala Met Asp Phe
        115                 120                 125

Trp Gly Gln Gly Thr Ser Val Thr Val Ser Ser Ala Thr Thr Thr Ala
    130                 135                 140

Pro Ser Val Ser Pro Trp Arg
145                 150

<210> SEQ ID NO 7
<211> LENGTH: 457
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggattttg ggctgatttt ttttattgtt gctcttttaa aaggggtcca gtgtgaggtg      60
aagcttctcg agtctggagg tggcctggtg cagcctggag atccctgaa actctcctgt      120 gcagcctcag gattcgattt tagtagatac tggatgagtt gggtccggca ggctccaggg      180
aaagggctag aatggattgg agaaattaat ccagatggca gtaagataaa ctatatgcca      240
tctctaaagg ataaattcat catctccaga gacaacgcca aaaatacgct gtacctgcaa      300
atgagcaaag tgagatctga ggacacagcc ctttattact gtgcaagacc tcggggttac      360
tacgctatgg acttctgggg tcaaggaacc tcagtcaccg tctcctcagc tacaacaaca      420
gccccacccg tctatccact ggtccctgaa gcttggg                              457

<210> SEQ ID NO 8
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<223> OTHER INFORMATION: See specification as filed for detailed
      description of substitutions and preferred embodiments

<400> SEQUENCE: 8

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Xaa
        35                  40                  45

Ser Arg Tyr Trp Met Ser Trp Val Arg Gln Ala Pro Gly Lys Gly Leu
    50                  55                  60
```

```
Glu Trp Ile Gly Glu Ile Asn Pro Asp Xaa Gly Ser Lys Ile Asn Tyr
 65                  70                  75                  80

Met Pro Ser Leu Lys Asp Lys Phe Ile Ile Ser Arg Asp Asn Ala Lys
                 85                  90                  95

Asn Thr Leu Tyr Leu Gln Met Ser Lys Val Arg Ser Glu Asp Thr Ala
            100                 105                 110

Leu Tyr Tyr Cys Ala Arg Pro Arg Gly Tyr Xaa Tyr Ala Met Asp Phe
        115                 120                 125

Trp Gly Gln Gly Thr Ser Val Thr Val Ser Ser Ala Thr Thr Thr Ala
    130                 135                 140

Pro Pro Val Tyr Pro Leu Val Pro Glu Ala Trp
145                 150                 155
```

<210> SEQ ID NO 9
<211> LENGTH: 449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atggattttg ggctgatttt ttttattgtt gctcttttaa aaggggtcca gtgtgaggtg      60
aagcttctcg agtctggagg tggcctggtg cagcctggag atccctgaa actctcctgt     120 gcagcctcag gattcgattt tagtagatac tggatgagtt gggtccggca ggctccaggg    180
aaagggctag aatggattgg agaaattaat ccagatagca gtaagataaa ctatatgcca    240
tctctaaagg ataaattcat catctccaga gacaacgcca aaaatacgct gtacctgcaa    300
atgagcaaag tgagatctga ggacacagcc ctttattact gtgcaagacc tcggggttac    360
tacgctatgg acttctgggg tcaaggaacc tcagtcaccg tctcctcagc tacaacaaca    420
gccccacccg tctatcccct ggcccctgg                                       449
```

<210> SEQ ID NO 10
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<223> OTHER INFORMATION: See specification as filed for detailed
      description of substitutions and preferred embodiments

<400> SEQUENCE: 10

```
Met Asp Phe Gly Leu Ile Phe Phe Ile Val Ala Leu Leu Lys Gly Val
  1               5                  10                  15

Gln Cys Glu Val Lys Leu Leu Glu Ser Gly Gly Gly Leu Val Gln Pro
             20                  25                  30

Gly Gly Ser Leu Lys Leu Ser Cys Ala Ala Ser Gly Phe Asp Phe Xaa
         35                  40                  45
```

```
Ser Arg Tyr Trp Met Ser Trp Val Arg Gln Ala Pro Gly Lys Gly Leu
 50                  55                  60

Glu Trp Ile Gly Glu Ile Asn Pro Asp Xaa Ser Ser Lys Ile Asn Tyr
 65                  70                  75                  80

Met Pro Ser Leu Lys Asp Lys Phe Ile Ile Ser Arg Asp Asn Ala Lys
                 85                  90                  95

Asn Thr Leu Tyr Leu Gln Met Ser Lys Val Arg Ser Glu Asp Thr Ala
                100                 105                 110

Leu Tyr Tyr Cys Ala Arg Pro Arg Gly Tyr Xaa Tyr Ala Met Asp Phe
                115                 120                 125

Trp Gly Gln Gly Thr Ser Val Thr Val Ser Ser Ala Thr Thr Thr Ala
                130                 135                 140

Pro Pro Val Tyr Pro Leu Ala Pro
145                 150
```

<210> SEQ ID NO 11
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<223> OTHER INFORMATION: See specification as filed for detailed
      description of substitutions and preferred embodiments

<400> SEQUENCE: 11

```
Met Asp Phe Gly Leu Ile Phe Phe Ile Val Ala Leu Leu Lys Gly Val
 1               5                  10                  15

Gln Cys Glu Val Lys Leu Leu Glu Ser Gly Gly Gly Leu Val Gln Pro
                 20                  25                  30

Gly Gly Ser Leu Lys Leu Ser Cys Ala Ala Ser Gly Phe Asp Phe Xaa
                 35                  40                  45

Ser Arg Tyr Trp Met Ser Trp Val Arg Gln Ala Pro Gly Lys Gly Leu
 50                  55                  60

Glu Trp Ile Gly Glu Ile Asn Pro Asp Xaa Ser Ser Lys Ile Asn Tyr
 65                  70                  75                  80

Met Pro Ser Leu Lys Asp Lys Phe Ile Ile Ser Arg Asp Asn Ala Lys
                 85                  90                  95

Asn Thr Leu Tyr Leu Gln Met Ser Lys Val Arg Ser Glu Asp Thr Ala
                100                 105                 110

Leu Tyr Tyr Cys Ala Arg Pro Arg Gly Tyr Xaa Tyr Ala Met Asp Phe
                115                 120                 125

Trp Gly Gln Gly Thr Ser Val Thr Val Ser Ser Ala Thr Thr Thr Ala
                130                 135                 140

Pro Ser Val Phe Pro Leu Ala
145                 150
```

<210> SEQ ID NO 12
<211> LENGTH: 435
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atggagtcac ataccaggt  ctttatattc gtgtttctct ggttgtctgg tgttgacgga      60
gacattgtga tgacccagtc tcacaaagtc atgtccacat cagtaggaga cagggtcagc     120
atcacctgca aggccagtca ggatgtgagt actgctgtag cctggcatca acagaaacca     180
ggacaatctc ctaaaccact gatttactcg gcatcctacc agtacactgg agtccctgat     240
cgcttcactg gcagtggatc tgggacggat ttcactttca ccatcagcag tgtgcaggct     300
gaagacctgg cagtttatta ctgtcagcaa cattacagta ttccgtggac gttcggtgga     360
ggcaccaagc tggaaatcaa acgggctgat gctgcaccaa ctgtatccat cttcccacca     420
tccagtaagc ttggg                                                      435
```

<210> SEQ ID NO 13
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<223> OTHER INFORMATION: See specification as filed for detailed
      description of substitutions and preferred embodiments

<400> SEQUENCE: 13

```
Met Glu Ser His Thr Gln Val Phe Ile Phe Val Phe Leu Trp Leu Ser
1               5                   10                  15

Gly Val Asp Gly Asp Ile Val Met Thr Gln Ser His Lys Val Met Ser
            20                  25                  30

Thr Ser Val Gly Asp Arg Val Ser Ile Thr Cys Lys Ala Ser Gln Asp
        35                  40                  45

Val Xaa Ser Thr Ala Val Ala Trp His Gln Gln Lys Pro Gly Gln Ser
    50                  55                  60

Pro Lys Pro Leu Ile Tyr Ser Ala Xaa Ser Tyr Gln Tyr Thr Gly Val
65                  70                  75                  80

Pro Asp Arg Phe Thr Gly Ser Gly Ser Gly Thr Asp Phe Thr Phe Thr
                85                  90                  95

Ile Ser Ser Val Gln Ala Glu Asp Leu Ala Val Tyr Tyr Cys Gln Gln
            100                 105                 110

His Tyr Ser Xaa Ile Pro Trp Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140
```

Ser Lys Leu Gly
145

<210> SEQ ID NO 14
<211> LENGTH: 435
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atggagacac agtctcaggt ctttgtattc gtgtttctct ggttgtctgg tgttgacgga      60
gacattgtga tgacccagtc tcacaaagtc atgtccacat cagtaggaga cagggtcagc     120
atcacctgca aggccagtca ggatgtgagt actgctgtag cctggcatca acagaaacca     180
ggacaatctc ctaaaccact gatttactcg gcatcctacc agtacactgg agtccctgat     240
cgcttcactg gcagtggatc tgggacggat tcactttca ccatcagcag tgtgcaggct     300
gaagacctgg cagtttatta ctgtcagcaa cattacagta ttccgtggac gttcggtgga     360
ggcaccaagc tggaaatcaa acgggctgat gctgcaccaa ctgtatccat cttcccacca     420
tccagtaagc ttggg                                                      435
```

<210> SEQ ID NO 15
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<223> OTHER INFORMATION: See specification as filed for detailed
      description of substitutions and preferred embodiments

<400> SEQUENCE: 15

Met Glu Thr Gln Ser Gln Val Phe Val Phe Val Phe Leu Trp Leu Ser
1               5                   10                  15

Gly Val Asp Gly Asp Ile Val Met Thr Gln Ser His Lys Val Met Ser
            20                  25                  30

Thr Ser Val Gly Asp Arg Val Ser Ile Thr Cys Lys Ala Ser Gln Asp
        35                  40                  45

Val Xaa Ser Thr Ala Val Ala Trp His Gln Gln Lys Pro Gly Gln Ser
    50                  55                  60

Pro Lys Pro Leu Ile Tyr Ser Ala Xaa Ser Tyr Gln Tyr Thr Gly Val
65                  70                  75                  80

Pro Asp Arg Phe Thr Gly Ser Gly Ser Gly Thr Asp Phe Thr Phe Thr
                85                  90                  95

Ile Ser Ser Val Gln Ala Glu Asp Leu Ala Val Tyr Tyr Cys Gln Gln
            100                 105                 110

His Tyr Ser Xaa Ile Pro Trp Thr Phe Gly Gly Gly Thr Lys Leu Glu
        115                 120                 125

```
Ile Lys Arg Ala Asp Ala Ala Pro Thr Val Ser Ile Phe Pro Pro Ser
    130                 135                 140

Ser Lys Leu Gly
145
```

<210> SEQ ID NO 16
<211> LENGTH: 422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
cccaggtctt tgtattggtg tttctctggt tgtctggtgt tgacggagac attgtgatga    60
cccagtctca caaagtcatg tccacatcag taggagacag ggtcagcatc acctgcaagg   120
ccagtcagga tgtgagtact gctgtagcct ggcatcaaca gaaaccagga caatctccta   180
aaccactgat ttactcggca tcctaccagt acactggagt ccctgatcgc ttcactggca   240
gtggatctgg gacggatttc actttcacca tcagcagtgt gcaggctgaa gacctggcag   300
tttattactg tcagcaacat tacagtattc cgtggacgtt cggtggaggc accaagctgg   360
aaatcaaacg ggctgatgct gcaccaactg tatccatctt cccaccatcc agtaagcttg   420
gg                                                                  422
```

<210> SEQ ID NO 17
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<223> OTHER INFORMATION: See specification as filed for detailed
      description of substitutions and preferred embodiments

<400> SEQUENCE: 17

```
Gln Val Phe Val Leu Val Phe Leu Trp Leu Ser Gly Val Asp Gly Asp
1               5                   10                  15

Ile Val Met Thr Gln Ser His Lys Val Met Ser Thr Ser Val Gly Asp
                20                  25                  30

Arg Val Ser Ile Thr Cys Lys Ala Ser Gln Asp Val Xaa Ser Thr Ala
            35                  40                  45

Val Ala Trp His Gln Gln Lys Pro Gly Gln Ser Pro Lys Pro Leu Ile
        50                  55                  60

Tyr Ser Ala Xaa Ser Tyr Gln Tyr Thr Gly Val Pro Asp Arg Phe Thr
65                  70                  75                  80

Gly Ser Gly Ser Gly Thr Asp Phe Thr Phe Thr Ile Ser Ser Val Gln
                85                  90                  95

Ala Glu Asp Leu Ala Val Tyr Tyr Cys Gln Gln His Tyr Ser Xaa Ile
```

```
                    100                 105                 110
Pro Trp Thr Phe Gly Gly Gly Thr Lys Leu Glu Ile Lys Arg Ala Asp
        115                 120                 125

Ala Ala Pro Thr Val Ser Ile Phe Pro Pro Ser Lys Leu Gly
        130                 135             140

<210> SEQ ID NO 18
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<223> OTHER INFORMATION: See specification as filed for detailed
      description of substitutions and preferred embodiments

<400> SEQUENCE: 18

Met Glu Ser Xaa Ser Gln Val Phe Val Phe Val Leu Trp Leu Ser
1               5                   10                  15

Gly Val Asp Gly Asp Ile Val Met Thr Gln Ser His Lys Val Met Ser
            20                  25                  30

Thr Ser Val Gly Asp Arg Val Ser Ile Thr Cys Lys Ala Ser Gln Asp
        35                  40                  45

Val Xaa Ser Thr Ala Val Ala Trp His Gln Gln Lys Pro Gly Gln Ser
    50                  55                  60

Pro Lys Pro Leu Ile Tyr Ser Ala Xaa Ser Tyr Gln Tyr Thr Gly Val
65                  70                  75                  80

Pro Asp Arg Phe Thr Gly Ser Gly Ser Gly Thr Asp Phe Thr Phe Thr
            85                  90                  95

Ile Ser Ser Val Gln Ala Glu Asp Leu Ala Val Tyr Tyr Cys Gln Gln
        100                 105                 110

His Tyr Ser Xaa Ile Pro Trp Thr Phe Gly Gly Gly Thr Lys Leu Glu
    115                 120                 125

Ile Lys Arg Ala Asp Ala Ala Pro Thr Val Ser Ile Phe Pro Pro Ser
        130                 135                 140

Ser Lys Leu Gly
145

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
```

```
<223> OTHER INFORMATION: Any amino acid
<220> FEATURE:
<223> OTHER INFORMATION: See specification as filed for detailed
      description of substitutions and preferred embodiments

<400> SEQUENCE: 19

Gly Phe Asp Phe Xaa Ser Arg Tyr Trp
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<223> OTHER INFORMATION: See specification as filed for detailed
      description of substitutions and preferred embodiments

<400> SEQUENCE: 20

Gln Asp Val Xaa Ser Thr Ala
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: See specification as filed for detailed
      description of substitutions and preferred embodiments

<400> SEQUENCE: 21

Ile Asn Pro Asp Xaa Ser Ser Lys Ile
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: See specification as filed for detailed
      description of substitutions and preferred embodiments

<400> SEQUENCE: 22

Ile Asn Pro Asp Xaa Gly Ser Lys Ile
1               5

<210> SEQ ID NO 23
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 23

Ser Ala Xaa Ser
1

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: See specification as filed for detailed
      description of substitutions and preferred embodiments

<400> SEQUENCE: 24

Ala Arg Pro Arg Gly Tyr Xaa Tyr Ala Met Asp Phe
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<223> OTHER INFORMATION: See specification as filed for detailed
      description of substitutions and preferred embodiments

<400> SEQUENCE: 25

Gln Gln His Tyr Ser Xaa Ile Pro Trp Thr
1               5                   10

<210> SEQ ID NO 26
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Ser Trp Val Arg Gln Ala Pro Gly Lys Gly Leu Glu
    50                  55                  60
```

Trp Ile Gly Glu Ile Asn Pro Asp Ser Ser Lys Ile Asn Tyr Met Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Pro Arg Gly Tyr Tyr Ala Met Asp Phe Trp Gly Gln
        115                 120                 125

Gly Thr Ser Val Thr Val Ser Ser Ala Thr Thr Ala Pro Ser Val
    130                 135                 140

Phe Pro Leu Ala
145

<210> SEQ ID NO 27
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Ser Trp Val Arg Gln Ala Pro Gly Lys Gly Leu Glu
    50                  55                  60

Trp Ile Gly Glu Ile Asn Pro Asp Ser Ser Lys Ile Asn Tyr Met Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Pro Arg Gly Tyr Tyr Ala Met Asp Phe Trp Gly Gln
        115                 120                 125

Gly Thr Ser Val Thr Val Ser Ser Ala Thr Thr Ala Pro Ser Val
    130                 135                 140

Phe Pro Leu Ala
145

<210> SEQ ID NO 28
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

```
Arg Tyr Trp Met Ser Trp Val Arg Gln Ala Pro Gly Lys Gly Leu Glu
         50                  55                  60

Trp Ile Gly Glu Ile Asn Pro Asp Ser Ser Lys Ile Asn Tyr Met Pro
 65                  70                  75                  80

Ser Leu Lys Asp Lys Phe Ile Ile Ser Arg Asp Asn Ala Lys Asn Thr
                 85                  90                  95

Leu Tyr Leu Gln Met Ser Lys Val Arg Ser Glu Asp Thr Ala Leu Tyr
            100                 105                 110

Tyr Cys Ala Arg Pro Arg Gly Tyr Tyr Ala Met Asp Phe Trp Gly Gln
           115                  120                 125

Gly Thr Ser Val Thr Val Ser Ser Ala Thr Thr Thr Ala Pro Ser Val
        130                 135                 140

Phe Pro Leu Ala
145

<210> SEQ ID NO 29
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Asp Phe Gly Leu Ile Phe Phe Ile Val Ala Leu Leu Lys Gly Val
 1               5                  10                  15

Gln Cys Glu Val Lys Leu Leu Glu Ser Gly Gly Gly Leu Val Gln Pro
             20                  25                  30

Gly Gly Ser Leu Lys Leu Ser Cys Ala Ala Ser Gly Phe Asp Phe Ser
         35                  40                  45

Arg Tyr Trp Met Ser Trp Val Arg Gln Ala Pro Gly Lys Gly Leu Glu
     50                  55                  60

Trp Ile Gly Glu Ile Asn Pro Asp Ser Ser Lys Ile Asn Tyr Met Pro
 65                  70                  75                  80

Ser Leu Lys Asp Lys Phe Ile Ile Ser Arg Asp Asn Ala Lys Asn Thr
                 85                  90                  95

Leu Tyr Leu Gln Met Ser Lys Val Arg Ser Glu Asp Thr Ala Leu Tyr
            100                 105                 110

Tyr Cys Ala Arg Pro Arg Gly Tyr Tyr Ala Met Asp Phe Trp Gly Gln
           115                  120                 125

Gly Thr Ser Val Thr Val Ser Ser Ala Thr Thr Thr Ala Pro Ser Val
        130                 135                 140

Ser Pro Trp Arg
145

<210> SEQ ID NO 30
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Phe Gly Leu Ile Phe Phe Ile Val Ala Leu Leu Lys Gly Val
 1               5                  10                  15

Gln Cys Glu Val Lys Leu Leu Glu Ser Gly Gly Gly Leu Val Gln Pro
             20                  25                  30
```

```
Gly Gly Ser Leu Lys Leu Ser Cys Ala Ala Ser Gly Phe Asp Phe Ser
            35                  40                  45

Arg Tyr Trp Met Ser Trp Val Arg Gln Ala Pro Gly Lys Gly Leu Glu
    50                  55                  60

Trp Ile Gly Glu Ile Asn Pro Asp Gly Ser Lys Ile Asn Tyr Met Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
                100                 105                 110

Tyr Cys Ala Arg Pro Arg Gly Tyr Tyr Ala Met Asp Phe Trp Gly Gln
                115                 120                 125

Gly Thr Ser Val Thr Val Ser Ser Ala Thr Thr Thr Ala Pro Pro Val
            130                 135                 140

Tyr Pro Leu Val Pro Glu Ala Trp
145                 150
```

<210> SEQ ID NO 31
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
            35                  40                  45

Arg Tyr Trp Met Ser Trp Val Arg Gln Ala Pro Gly Lys Gly Leu Glu
    50                  55                  60

Trp Ile Gly Glu Ile Asn Pro Asp Ser Ser Lys Ile Asn Tyr Met Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
                100                 105                 110

Tyr Cys Ala Arg Pro Arg Gly Tyr Tyr Ala Met Asp Phe Trp Gly Gln
                115                 120                 125

Gly Thr Ser Val Thr Val Ser Ser Ala Thr Thr Thr Ala Pro Pro Val
            130                 135                 140

Tyr Pro Leu Ala Pro
145
```

<210> SEQ ID NO 32
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Met Asp Phe Gly Leu Ile Phe Phe Ile Val Ala Leu Leu Lys Gly Val
1               5                   10                  15
```

```
Gln Cys Glu Val Lys Leu Leu Glu Ser Gly Gly Gly Leu Val Gln Pro
             20                  25                  30

Gly Gly Ser Leu Lys Leu Ser Cys Ala Ala Ser Gly Phe Asp Phe Ser
         35                  40                  45

Arg Tyr Trp Met Ser Trp Val Arg Gln Ala Pro Gly Lys Gly Leu Glu
     50                  55                  60

Trp Ile Gly Glu Ile Asn Pro Asp Ser Ser Lys Ile Asn Tyr Met Pro
65                  70                  75                  80

Ser Leu Lys Asp Lys Phe Ile Ile Ser Arg Asp Asn Ala Lys Asn Thr
                 85                  90                  95

Leu Tyr Leu Gln Met Ser Lys Val Arg Ser Glu Asp Thr Ala Leu Tyr
            100                 105                 110

Tyr Cys Ala Arg Pro Arg Gly Tyr Tyr Ala Met Asp Phe Trp Gly Gln
        115                 120                 125

Gly Thr Ser Val Thr Val Ser Ser Ala Thr Thr Thr Ala Pro Ser Val
    130                 135                 140

Phe Pro Leu Ala
145

<210> SEQ ID NO 33
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Glu Ser His Thr Gln Val Phe Ile Phe Val Phe Leu Trp Leu Ser
1               5                   10                  15

Gly Val Asp Gly Asp Ile Val Met Thr Gln Ser His Lys Val Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp His Gln Gln Lys Pro Gly Gln Ser Pro
    50                  55                  60

Lys Pro Leu Ile Tyr Ser Ala Ser Tyr Gln Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Ser Ile Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Lys Leu
    130                 135                 140

Gly
145

<210> SEQ ID NO 34
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

```
Met Glu Thr Gln Ser Gln Val Phe Val Phe Val Leu Trp Leu Ser
1               5                   10                  15

Gly Val Asp Gly Asp Ile Val Met Thr Gln Ser His Lys Val Met Ser
                20                  25                  30

Thr Ser Val Gly Asp Arg Val Ser Ile Thr Cys Lys Ala Ser Gln Asp
            35                  40                  45

Val Ser Thr Ala Val Ala Trp His Gln Gln Lys Pro Gly Gln Ser Pro
    50                  55                  60

Lys Pro Leu Ile Tyr Ser Ala Ser Tyr Gln Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
                100                 105                 110

Ser Ile Pro Trp Thr Phe Gly Gly Gly Thr Lys Leu Glu Ile Lys Arg
            115                 120                 125

Ala Asp Ala Ala Pro Thr Val Ser Ile Phe Pro Pro Ser Ser Lys Leu
            130                 135                 140

Gly
145

<210> SEQ ID NO 35

<400> SEQUENCE: 35

000

<210> SEQ ID NO 36
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Phe Val Leu Val Phe Leu Trp Leu Ser Gly Val Asp Gly Asp
1               5                   10                  15

Ile Val Met Thr Gln Ser His Lys Val Met Ser Thr Ser Val Gly Asp
                20                  25                  30

Arg Val Ser Ile Thr Cys Lys Ala Ser Gln Asp Val Ser Thr Ala Val
            35                  40                  45

Ala Trp His Gln Gln Lys Pro Gly Gln Ser Pro Lys Pro Leu Ile Tyr
    50                  55                  60

Ser Ala Ser Tyr Gln Tyr Thr Gly Val Pro Asp Arg Phe Thr Gly Ser
65                  70                  75                  80

Gly Ser Gly Thr Asp Phe Thr Phe Thr Ile Ser Ser Val Gln Ala Glu
                85                  90                  95

Asp Leu Ala Val Tyr Tyr Cys Gln Gln His Tyr Ser Ile Pro Trp Thr
                100                 105                 110

Phe Gly Gly Gly Thr Lys Leu Glu Ile Lys Arg Ala Asp Ala Ala Pro
            115                 120                 125

Thr Val Ser Ile Phe Pro Pro Ser Ser Lys Leu Gly
            130                 135                 140

<210> SEQ ID NO 37
<211> LENGTH: 145
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid

<400> SEQUENCE: 37

Met Glu Ser Xaa Ser Gln Val Phe Val Phe Val Phe Leu Trp Leu Ser
1               5                   10                  15

Gly Val Asp Gly Asp Ile Val Met Thr Gln Ser His Lys Val Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp His Gln Gln Lys Pro Gly Gln Ser Pro
    50                  55                  60

Lys Pro Leu Ile Tyr Ser Ala Ser Tyr Gln Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Ser Ile Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Lys Leu
    130                 135                 140

Gly
145

<210> SEQ ID NO 38
<211> LENGTH: 444
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggattttg ggctgatttt ttttattgtt gctcttttaa aaggggtcca gtgtgaggtg     60
aagcttctcg agtctggagg tggcctggtg cagcctggag gatccctgaa actctcctgt    120
gcagcctcag gattcgattt tagtagatac tggatgagtt gggtccggca ggctccaggg    180
aaagggctag aatggattgg agaaattaat ccagatagca gtaagataaa ctatatgcca    240
tctctaaagg ataaattcat catctccaga gacaacgcca aaaatacgct gtacctgcaa    300
atgagcaaag tgagatctga ggacacagcc ctttattact gtgcaagacc tcgaggttac    360
tacgctatgg acttctgggg tcaaggaacc tcagtcaccg tctcctcagc tacaacaaca    420
gccccatcgg tctccccctg cgc                                            444

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (8)..(8)
<223> OTHER INFORMATION: Any amino acid

<400> SEQUENCE: 39

Ala Leu Phe Ala Leu Ala Lys Xaa Val
1               5
```